US007148061B2

(12) United States Patent
Lenardo et al.

(10) Patent No.: US 7,148,061 B2
(45) Date of Patent: Dec. 12, 2006

(54) IDENTIFICATION OF A NOVEL DOMAIN IN THE TUMOR NECROSIS FACTOR RECEPTOR FAMILY THAT MEDIATES PRE-LIGAND RECEPTOR ASSEMBLY AND FUNCTION

(75) Inventors: Michael J. Lenardo, Bethesda, MD (US); Francis Ka-Ming Chan, Silver Spring, MD (US); Richard M. Siegel, Washington, DC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 289 days.

(21) Appl. No.: 10/203,495

(22) PCT Filed: Feb. 9, 2001

(86) PCT No.: PCT/US01/04125

§ 371 (c)(1),
(2), (4) Date: Aug. 9, 2002

(87) PCT Pub. No.: WO01/58953

PCT Pub. Date: Aug. 16, 2001

(65) Prior Publication Data

US 2003/0108992 A1    Jun. 12, 2003

Related U.S. Application Data

(60) Provisional application No. 60/181,909, filed on Feb. 11, 2000.

(51) Int. Cl.
*C12N 5/10* (2006.01)
*C07K 14/715* (2006.01)

(52) U.S. Cl. .................. 435/325; 435/230.1; 435/69.1; 435/69.7; 530/350; 424/185.1; 424/192.1; 536/23.4; 536/23.5

(58) Field of Classification Search ................ 530/350; 514/12
See application file for complete search history.

(56) References Cited

U.S. PATENT DOCUMENTS

| 5,503,995 | A   | 4/1996  | Khudyakov et al. |
|-----------|-----|---------|------------------|
| 5,545,806 | A   | 8/1996  | Lonberg et al. |
| 5,569,825 | A   | 10/1996 | Lonberg et al. |
| 5,625,126 | A   | 4/1997  | Lonberg et al. |
| 5,633,145 | A * | 5/1997  | Feldmann et al. ......... 435/69.1 |
| 5,633,425 | A   | 5/1997  | Lonberg et al. |
| 5,661,016 | A   | 8/1997  | Lonberg et al. |
| 5,770,429 | A   | 6/1998  | Lonberg et al. |
| 5,789,650 | A   | 8/1998  | Lonberg et al. |
| 5,814,318 | A   | 9/1998  | Lonberg et al. |
| 5,830,731 | A   | 11/1998 | Seed et al. |
| 5,866,372 | A   | 2/1999  | Stein et al. |
| 6,569,664 | B1* | 5/2003  | Gatanaga et al. ........... 435/226 |

FOREIGN PATENT DOCUMENTS

| JP | 07/289266    | 11/1995 |
|----|--------------|---------|
| JP | WO 96/20206  | 7/1996  |
| WO | WO 95/21915  | 8/1995  |
| WO | WO 98/01555  | 1/1998  |
| WO | WO 98/18824  | 5/1998  |
| WO | WO 99/11791  | 3/1999  |
| WO | WO 99/38525  | 8/1999  |

OTHER PUBLICATIONS

Ashkenazi and Dixit, "Death Receptors: Signaling and Modulation," *Science* 281:1305-1308 (Aug. 28, 1998).
Banner et al., "Crystal Structure of the Soluble Human 55 kd TNF Receptor-Human TNFβ Complex: Implications for TNF Receptor Activation," *Cell* 73(3):431-435 (May 7, 1993).
Blezinger et al., "Systemic inhibition of tumor growth and tumor metastases by intramuscular administration of the endostatin gene," *Nat. Biotechnol.* 17(4):343-348 (Apr. 1999).
Blondelle et al., "Rapid identification of compounds with enhanced antimicrobial activity by using conformationally defined combinatorial libraries," *Biochem. J.* 313:141-147 (1996).

(Continued)

*Primary Examiner*—Eileen B. O'Hara
(74) *Attorney, Agent, or Firm*—Needle & Rosenberg, P.C.

(57) ABSTRACT

The present invention provides a polypeptide comprising the isolated amino acid sequence of a pre-ligand assembly domain (PLAD) of a TNF-like receptor. Also provided by this invention is a polypeptide comprising the isolated amino acid sequence of a pre-ligand assembly domain (PLAD), wherein the PLAD is selected from the group consisting of: the PLAD of a TNF-R, the PLAD of p60, the PLAD of p80, the PLAD of Fas (CD95/APO-1), the PLAD of TRAIL receptors, the PLAD of LTβR, the PLAD of CD40, the PLAD of CD30, the PLAD of CD27, the PLAD of HVEM, the PLAD of OX40 and the PLAD of DR4. TNF-R, p60, p80, Fas, TRAIL receptor, LTβR, CD40, CD30, CD27, HVEM, OX40, DR4, TROY, EDAR, XEDAR, DCR3, AITR, 4-1BB, DR3, RANK, TACI, BCMA, DR6, DPG, DR5, DCR1 AND DCR2 are all members of the TNF receptor superfamily or the TNF-like receptor family. The invention also provides the PLAD for other members of the TNF receptor superfamily. The polypeptides of the present invention can be utilized to inhibit oligomerization of members of the TNF receptor superfamily. These polypeptides can also be utilized to inhibit ligand binding to members of the TNF receptor superfamily. The present invention also provides a composition comprising an inhibitor of TNF receptor oligomerization. Further provided by this invention are members of the TNF receptor superfamily that are lacking a PLAD.

25 Claims, 20 Drawing Sheets

OTHER PUBLICATIONS

Boldin et al., "Self-association of the "Death Domains" of the p55 Tumor Necrosis Factor (TNF) Receptor and Fas/APO1 Prompts Signaling for TNF and Fas/APO1 Effects," *J. Biol. Chem.* 270(1):387-391 (1995).

Boldin et al., "A Novel Protein That Interacts with the Death Domain of Fas/APO1 Contains a Sequence Motif Related to the Death Domain," *J. Biol. Chem.* 270:7795-7798 (1995).

Boldin et al., "Involvement of MACH, a Novel MORT1/FADD-Interacting Protease, in Fas/APO-1- and TNF Receptor-Induced Cell Death," 85:803-815 (Jun. 14, 1996).

Chan et al., "A Domain in TNF Receptors That Mediates Ligand-Independent Receptor Assembly and Signaling," *Science* 288(5475):2351-2354 (Jun. 30, 2000).

Chen et al., "Mapping the Domain(s) Critical for the Binding of Human Tumor Necrosis Factor-α to Its Two Receptors," *J. Biol. Chem.* 270(6):2874-2878 (1995).

Chinnaiyan et al., "FADD, a Novel Death Domain-Containing Protein, Interacts with the Death of Fas and Initiates Apoptosis," *Cell* 81(4):505-512 (May 19, 1995).

Corcoran e tal., "Characterization of ligand binding by the human p55 tumour-necrosis-factor receptor. Involvement of individual cysteine-rich repeats," *Eur. J. Biochem.* 223:831-840 (1994).

Cosma et al., "Mutations in the Extracellular Domain Cause RET Loss of Function by a Dominant Negative Mechanism," *Mol. Cell. Biol.* 18(6):3321-3329 (1998).

Declercq et al., "Cooperation of Both TNF Receptors in Inducing Apoptosis: Involvement of the TNF Receptor-Associated Factor Binding Domain of the TNF Receptor 75," *J. Immunol.* 161:390-399 (1998).

Dörner et al., "The Synthesis of Peptidomimetic Combinatorial Libraries Through Successive Amide Alkylations," *Bioorg. Med. Chem.* 4(5):709-715 (May 1996).

Drappa et al., "*Fas* Gene Mutations In The Canale-Smith Syndrome, An Inherited Lymphoproliferative Disorder Associated With Autoimmunity," *N. Engl. J. Med.* 335(22):1643-1649 (Nov. 28, 1996).

Eichler et al., "Peptide, Peptidomimetic, and Organic Synthesis Combinatorial Libraries," *Med Res Rev* 15(6):481-496 (Nov. 1995).

Fakhral et al., "Construction and Characterization of Retroviral Vectors for Interleukin-2 Gene Therapy," *J. Immunother* 20(6):437-448 (1997).

Fisher et al., "Dominant Interfering Fas Gene Mutations Impair Apoptosis in a Human Autoimmune Lymphoproliferative Syndrome," *Cell* 81(6):935-946 (Jun. 16, 1995).

Gadella et al., "Oligomerization of Epidermal Growth Factor Receptors on A431 Cells Studied by Time-resolved Flourescence Imaging Microscopy. A Stereochemical Model for Tyrosine Kinase Receptor Activation," *J. Cell. Biol.* 129(6):1543-1558 (Jun. 1995).

Gorman et al., "A recombinant adenovirus that directs secretion of biologically active κ-bungarotoxin from mammalian cells," *Bran Res. Mol. Brain Res.* 44(1):143-146 (1997).

Guo et al., "Fluorescence Resonance Energy Transfer Reveals Interleukin (IL)-1-dependent Aggregation of IL-1 Type I Receptors That Correlates with Receptor Activation," *J. Biol. Chem* 270(46):27562-27568 (Nov. 17, 1995).

Haridas et al., "Overexpression of the p80 TNF Receptor Leads to TNF-Dependent Apoptosis, Nuclear Factor-κB Activation, and c-Jun Kinase Activation," *J. Immunol.* 160:3152-3162 (1998).

Heller et al., "The p70 Tumor Necrosis Factor Receptor Mediates Cytotoxicity," *Cell* 70(1):47-56 (Jul. 10, 1992).

Herskowitz, "Functional inactivation of genes by dominant negative mutations," *Nature* 329(6136):219-222 (Sep. 17, 1987).

Horie and Watanabe, "CD30: expression and function in health and disease," *Semin. Immunol.* 10(6):457-470 (Dec. 1998).

Hsu et al., "Differential Expression and Ligand Binding Properties of tumor necrosis factor receptor chimeric mutants," *J. Biol. Chem.* 268(22):16430-16436 (1993).

Hsu et al., "TNF-Dependent Recruitment of the Protein Kinase RIP to the TNF Receptor-1 Signaling Complex," *Immunity* 4:387-396 (1996).

Huang et al., "NMR structure and mutagenesis of the Fas (APO-1/CD95) death domain," *Nature* 384(6640):638-641.

Hughes et al., "Delivery of a Secretable Adenosine Deainase Through Microcapsules—A Novel Approach to Somatic Gene Therapy," *Hum. Gene Ther.* 5(12):1445-1455 (Dec. 1994).

Hymowitz et al., "Triggering Cell Death: The Crystal Structure of Apo2l/TRAIL in a Complex with Deatch Receptor 5," *Mol. Cell* 4:563-571 (Oct. 1999).

Jackson et al., "Autoimmune Lymphoproliferative Syndrome with Defective Fas: Genotype Influences Penetrance," *Am. J. Hum. Genet.* 64:1002-1014 (Apr. 1999).

Jiang et al., "Prevention of Constitutive TNF Receptor 1 Signaling by Silencer of Death Domains," *Science* 283(5401):543-546 (Jan. 22, 1999).

Jones et al., "TNF Recruits TRADD to the Plasma Membrane But Not the trans-Golgi Network, the Principal Subcellular Location of TNF-R1," *J. Immunol.* 162:1042-1048 (1999).

Jouanguy et al., "A human *IFNGR1* small deletion hotspot associated with dominant susceptibility to mycobacterial infection," *Nat. Genet.* 21(4):370-378 (Apr. 1999).

Kischkel et al., "Cytotoxicity-dependent APO-1 (Fas/CD95)-associated proteins form a death-inducing signaling complex (DISC) with the receptor," *EMBO J.* 14(22):5579-5588 (1995).

Klaus et al., "CD40: A Pivotal Receptor in the Determination of Life/Death Decisions in B Lymphcytes," *Int. Rev. Immunol.* 15(1-2):5-31 (1997).

Lenardo et al., "Mature T Lymphocyte Apoptosis—Immune Regulation in a Dynamic and Unpredictable Antigenic Environment," *Ann. Rev. Immunol.* 17:221-253 (1999).

Leonardo, "Molecular Regulation of Lymphocyte Apoptosis, pp. 595-596. In: Strauss SE, moderator. An Inherited Disorder of Lymphocyte Apoptosis: The Autoimmune Lymphoproliferative Syndrome," *Ann. Intern. Med.* 130(7):591-601 (1999).

Levy-Toledano et al., "Investigation of the mechanism of the dominant negative effect of mutations in the tyrosine kinase domain of the insulin receptor," *EMBO J.* 13(4):835-842 (1994).

Li and Schlessinger, "Platelet-Derived Growth Factor (PDGF)-Induced Disulfide-Linked Dimerization of PDGF Receptor in Living Cells," *Mol. Cell. Biol.* 11(7):3756-3761 (Jul. 1991).

Li and Stanley, "Role of dimerization and modification of the CSF-1 receptor in its activation and internalization during the CSF-1 response," *EMBO J.* 10(2):277-288 (1991).

Linvah et al., "Crystallographic Evidence for Preformed Dimers of Erythropoietin Receptor Before Ligand Activation," *Science* 283(5404):987-990 (Feb. 12, 1999).

Loetscher et al., "Recombinant 55-kDa tumor necrosis factor (TNF) receptor," *J. Biol. Chem.* 266(27):18324-18329 (1991).

Mahajan et al., "Novel mutant green fluorescent protein protease substrates reveal the activation of specific caspases during apoptosis," *Chem. Biol.* 6(6):401-409 (Jun. 1999).

Marsters et al., "Identification of cysteine-rich domains of the type 1 tumor necrosis factor receptor involved in ligand binding," *J. Biol. Chem.* 267:5747-5750 (1992).

Martin et al., "Membrane Oligomerization and Cleavage Activates the Caspases-8 (FLICE/MACH [alpha ] 1) Death Signal," *J. Biol. Chem.* 273(8):4345-4349 (1998).

Martin et al., "Defective CD95/APO-1/Fas signal complex formation in the human autoimmune lymphoproliferative syndrome, type Ia," *Proc. Natl. Acad. Sci* 96:4552-4557 (Apr. 1999).

Mongkolsapaya et al., "Structure of the TRAIL-DR5 complex reveals mechanisms conferring specificity in apoptotic initiation," *Nat Struct. Biol.* 6(11):1048-1053 (Nov. 1999).

Muzio et al., "FLICE, A Novel FADD-Homologous ICE/CED-3-like Protease, Is Recruited to the CD95 (Fas/APO-1) Death-Inducing Signaling Complex," *Cell* 85(6):817-822 (Jun. 14, 1996).

Naismith et al., "Structures of the extracellular domain of the type I tumor necrosis factor receptor," *Structure* 4(11):1251-1262 (Nov. 15, 1996).

Naismith et al., "Seeing Double: Crystal Structures of the Type I TNF Receptor," *J. Mol. Recog.* 9:113 (1995).

Naismith et al., "Crystallographic Evidence for Dimerization of Unliganded Tumor Necrosis Factor Receptor," *J. Biol. Chem.* 270(22):13303-13307 (1995).

Naismith and Sprang, "Modularity in the TNF-receptor family," *TIBS* 23(2):74-79 (Feb. 1998).

Nicholson and Thornberry, "Caspases: killer proteases," *TIBS* 22(8):299-306 (Aug. 1997).

Orlinick et al., "Separate Domains of the Human Fas Ligand Dictate Self-association and Receptor Binding," *J. Biol. Chem.* 272:288-289 (1997).

Ostresh et al., "Libraries from libraries"; Chemical transformation of combinatorial libraries to extend the range and repertoire of chemical diversity, *Proc. Natl. Acad. Sci* 91(23):11138-11142 (Nov. 8, 1994).

Papoff et al., "Identification and Characterization of a Ligand-Independent Oligomerization Domain in the Extracellular Region of the CD95 Death Receptor," *J. Biol. Chem.* 274(53):38241-38250 (Dec. 31, 1999).

Papoff et al., "An N-Terminal Domain Shared by Fas/Apo-1 (CD95) Soluble Variants Prevents Cells Death In Vitro," *J. Immunol.* 156(12):4622-4630 (Jun. 15, 1996).

Perez-Paya et al., "Functionalized Protein-like Structures from Conformationally Defined Synthetic Combinatorial Libraries," *J. Biol. Chem.* 271(8):4120-4126 (1996).

Pinckard et al., "Ligand-induced Formation of p55 and p75 Tumor Necrosis Factor Receptor Heterocomplexes on Intact Cells," *J. Biol. Chem.* 272(16):10784-10789 (Apr. 18, 1997).

Pollock and Heim, "Using GFP in FRET-based applications," *Trends Cell Biol.* 9:57-60 (Feb. 1999).

Rade et al., "Retroviral vector-mediated expression of hirudin by human vascular endothelial cells: implications for the design of retroviral vectors expressing biologically active proteins," *Gene Ther.* 6:385-392 (Mar. 1999).

Reid et al., "Mechanisms of Tumor Necrosis Factor Cytotoxicity and the Cytotoxic Signals Transduced by the p75-Tumor Necrosis Factor Receptor," *Circ. Shock* 44(2):84-90 (Oct. 1994).

Remy et al., "Erythropoietin Receptor Activation by a Ligand-Induced Conformation Change," *Science* 283:990-993 (Feb. 12, 1999).

Rieux-Laucat et al., "Mutations in Fas Associated with Human Lymphoproliferative Syndrome and Autoimmunity," *Science* 268(5215):1347-1349 (Jun. 2, 1995).

Schievella et al., "MADD, a Novel Death Domain Protein That Interacts with the Type 1 Tumor Necrosis Factor Receptor and Activates Mitogen-activated Protein Kinase," *J. Biol. Chem.* 272(18):12069-12075 (1997).

Shu et al., "The tumor necrosis factor receptor 2 signal transducers TRAF2 and c-IAP1 are components of the tumor necrosis factor receptor 1 signaling complex," *Proc. Natl. Acad. Sci.* 93:13973-13978 (1996).

Siegel et al., "Fas Preassociations Required for Apoptosis Signaling and Dominant Inhibition by Pathogenic Mutations," *Science* 288:2354-2357 (Jun. 30, 2000).

Smith et al., "The TNF Receptor Superfamily of Cellular and Viral Proteins: Activation, Costimulation, and Death," *Cell* 76(6):959-962 (Mar. 25, 1994).

Starling et al., "Identification of Amino Acid Residues Important for Ligand Binding to Fas," *J. Exp. Med* 185(8):1487-1492 (Apr. 21, 1997).

Szöllösi et al., "Fluorescence Energy Transfer Measurements on Cell Surfaces: A Critical Comparison of Steady-State Fluorimetric and Flow Cytometric Methods," *Cytometry* 5(2):210-216 (Jan. 1984).

Tartaglia et al., "Tumor necrosis factor receptor signaling," *J. Biol. Chem.* 267:4304-4307 (1992).

Ting et al., "RIP mediated tumor necrosis factor receptor 1 activation of NF-κB but not Fas/APO-1-initiated apoptosis," *EMBO J.* 15(22):6189-6199 (Nov. 15, 1996).

Tracey and Cerami, "Tumor Necrosis Factor: A Pleiotropic Cytokine and Therapeutic Target," *Ann. Rev. Med.* 45:491-503 (1994).

Tracey et al., "Tumor Necrosis Factor, Other Cytokines and Disease," *Ann. Rev. Cell Biol.* 9:317-343 (1993).

Trón et al., "Flow Cytometric Measurement of Fluorescence Resonance Energy Transfer on Cell Surfaces. Quantitative Evaluation of the transfer Efficiency on a Cell-by-Cell Basis," *Biophys J.* 45:939-946 (May 1984).

Tsien, "The Green Flourescence Protein," *Ann. Rev. Biochem.* 67:509-544 (1998).

Ueno et al., "Adenovirus-Mediated Expression of the Secreted Form of Basic Fibroblast Growth Factor (FGF-2) Induces Cellular Proliferation and Angiogenesis In Vivo," *Aterioscler. Thromb. Vasc. Biol.* 17:2453-2460 (1997).

Vaishnaw et al., "The molecular basis for apoptotic defects in patients with CD95 (Fas/Apo-1) mutations," *J. Clin. Invest.* 103(3):355-363 (1999).

Wajant et al., "Tumor Necrosis Factors in 1998," *Cytokine & Growth Factor Rev.* 9(3-4):297-302 (Sep./Dec. 1998).

Walczak, "Tumoricidal activity of tumor necrosis factor-related apoptosis-inducing ligand *in vivo*," *Nat. Med.* 5(2):157-163 (Feb. 1999).

Wallach et al., "Tumor Necrosis Factor Receptor and Fas Signaling Mechanisms," *Ann. Rev. Immunol.* 17:331-367 (1999).

Weiss et al., "Enhancement of TNF Receptor p60-Mediated Cytotoxicity by TNF Receptor p80," *J. Immunol.* 158(5):2398-2404 (Mar. 1, 1997).

Deng et al. Amelioration of inflammatory arthritis by targeting the pre-ligand assembly domain of tumor necrosis factor receptors. *Nature Medicine,* pp. 1-7, published online Sep. 18, 2005.

* cited by examiner

| | | | |
|---|---|---|---|
| p60 | 44 | CPQG—KYIHPQNNSICCTKCHKGTYLYNDCPGPGQD—TDC | 82 |
| p80 | 40 | CR—LREYYDQTAQ-MCCSKCSPGQHAKVFC-TKTSD—TVC | 76 |
| LTβR | 43 | CRDQEKEYYEPQHR-ICCSRCPPGTYVSAKC-SRIRD—TVC | 81 |
| CD40 | 26 | CREK—QY—LINS-QCCSLCQPGQKLVSDC-TEFTE—TEC | 60 |
| HVEM | 42 | CKED—EY—PVGS-ECCPKCSPGYRVKEAC-GELTG—TVC | 76 |
| CD30 | 29 | CHGNPSHYYDKAVRR-CCYRCPMGLFPRQQCPQRPTDCRKQC | 70 |

Pt 1:   RLSSKSVNAQVTDINSKGLELRKTVTVETQNLEGLHHDGQFCHKPCPPGERKARDCTVNGD*NQTACPLPNAEDVDCVMKDMA.*
Pt 20:  RLSSKSVNAQVTDINSKGLELRKTVTVETQNLEGLHHDGQFCHKPCPPGERKARD.

US 7,148,061 B2

IDENTIFICATION OF A NOVEL DOMAIN IN THE TUMOR NECROSIS FACTOR RECEPTOR FAMILY THAT MEDIATES PRE-LIGAND RECEPTOR ASSEMBLY AND FUNCTION

U.S. Provisional Application No. 60/181,909, filed on Feb. 11, 2000, is hereby incorporated by reference in its entirety.

BACKGROUND OF THE INVENTION

1. Field of the Invention

This invention provides a novel function for a conserved domain in the extracellular region of the members of the TNF receptor (TNFR) superfamily in mediating specific ligand-independent assembly of receptor oligomers.

2. Background Art

The members of the TNFR superfamily typically contain one to six cysteine rich domains in their extracellular regions, a single transmembrane domain and variably sized intracytoplasmic domains. The members of this receptor family typically bind to ligands of the TNF cytokine family that are defined by structural, functional and sequence similarities. These receptors form trimers in their active liganded state and several members contain a cytoplasmic domain referred to as a death domain. According to the present invention, the extracellular region of these receptors is further characterized by a novel self-association or homotypic association function that is mediated via a pre-ligand receptor assembly domain (PLAD) that contains at least one cysteine rich domain More specifically, members of the TNFR superfamily, including TRAIL receptor 1, CD40, 60 kDa TNFR and 80 kDa TNFR show this homotypic association. Other members of the TNFR superfamily, including Fas, LTβR, CD40, CD30, CD27, HVEM, RANK, OX40 and DR4 contain this PLAD. The PLAD is necessary for ligand binding and receptor function. Thus, members of the TNFR superfamily appear to signal through distinct pre-formed complexes rather than through ligand-induced cross-linking of individual receptor subunits. Therefore, PLAD can be targeted by pharmaceutical agents in order to block the formation of these preformed complexes and thus block receptor function.

SUMMARY OF THE INVENTION

The present invention provides a polypeptide comprising the isolated amino acid sequence of a pre-ligand assembly domain (PLAD) of a TNF-like receptor.

Also provided by this invention is a polypeptide comprising the isolated amino acid sequence of a pre-ligand assembly domain (PLAD), wherein the PLAD is selected from the group consisting of: the PLAD of TNF-R, the PLAD of p60, the PLAD of p80, the PLAD of Fas (CD95/APO-1), the PLAD of TRAIL receptors, the PLAD of LTβR, the PLAD of CD40, the PLAD of CD30, the PLAD of CD27, the PLAD of HVEM, the PLAD of OX40 and the PLAD of DR4. TNF-R, p60 TNFR, p80 TNFR, Fas, TRAIL receptors, LTβR, CD40, CD30, CD27, HVEM, OX40 an DR4 are all members of the TNF receptor superfamily also referred to herein as the TNF-like receptor family. The invention also provides the PLAD for other members of the TNF receptor superfamily and how it can be identified by one of skill in the art.

The polypeptides of the present invention can be utilized to inhibit PLAD self-association as well as oligomerization of members of the TNF receptor superfamily. These polypeptides can also be utilized to inhibit ligand binding to members of the TNF receptor superfamily.

The present invention also provides a composition comprising an inhibitor of TNF receptor oligomerization. Further provided by this invention are members of the TNF receptor superfamily that are lacking a PLAD.

DETAILED DESCRIPTION OF THE INVENTION

Figure 1A:
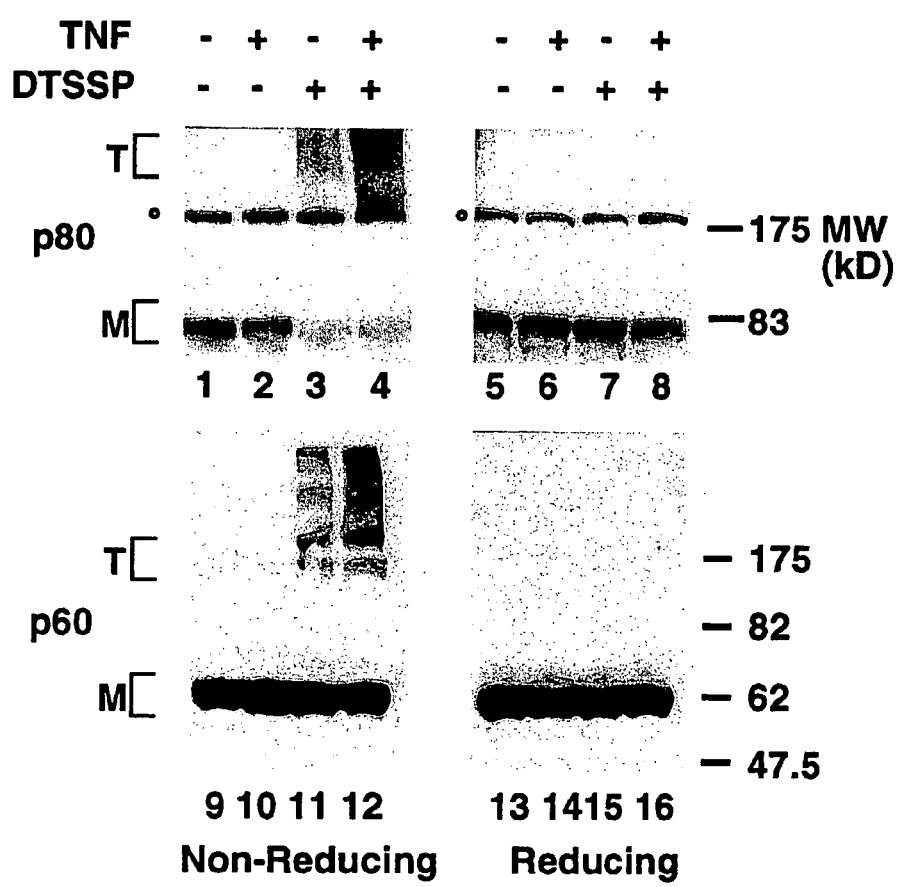
FIG. 1A illustrates TNFR oligomers in the absence of ligand. H9 T cell lymphoma, treated or untreated with TNFα, were subjected to crosslinking with DTSSP (7). Total cell lysates were electrophoresed under non-reducing (lanes 1–4, 9–12) or reducing (lanes 5–8, 13–16) conditions as indicated and blotted for p60 or p80 TNFRs. The brackets indicate the position of trimers (T) and monomers (M). The circles indicate a non-specific protein cross-reacting with the anti-p80 antibody. The results represent three independent experiments.

The present invention may be understood more readily by reference to the following detailed description of the preferred embodiments of the invention and the Examples included therein and to the Figures and their previous and following description.

As used in the specification and in the claims, "a" can mean one or more, depending upon the context in which it is used. Thus, for example, reference to "a nucleic acid" means that at least one nucleic acid is utilized.

Polypeptides

The present invention provides a polypeptide comprising the isolated amino acid sequence of a pre-ligand assembly domain (PLAD). The present invention also provides a polypeptide consisting of the amino acid sequence of a pre-ligand assembly domain. The PLAD of the present invention can be the PLAD of a TNF-R, the PLAD of p60, the PLAD of p80, the PLAD of Fas (CD95/APO-1), the PLAD of TRAIL, the PLAD of LTβR, the PLAD of CD40, the PLAD of CD30, the PLAD of CD27, the PLAD of HVEM, the PLAD of OX40, the PLAD of DR4 or any other PLAD domain from a member of the TNFR superfamily. Since the PLAD domain is highly conserved among members of the TNFR superfamily, one skilled in the art could identify the PLAD domain of any TNF receptor by searching available databases for the conserved motif that characterizes the PLAD domain. Identification of these regions in TNF-like receptors is made routine by the provision of exemplary PLAD sequences herein and their comparison to published sequences of other members of the family (see FIG. 3, for example). Furthermore, one skilled in the art would also be able to identify a PLAD by performing functional assays, such as those provided in the Examples.

The present invention also provides a polypeptide of 50 to 125 amino acids comprising an isolated PLAD, wherein the polypeptide comprises the subsequence $R_1$-TNF-like receptor PLAD-R$_2$, wherein R$_1$ and R$_2$ are optional and when present can be H, acyl, NH$_2$, an amino acid or a peptide. When present, R$_1$ and/or R$_2$ can be any amino acid. When R$_1$ and/or R$_2$ is a peptide, this peptide can vary in length. For example, R$_1$ and/or R$_2$ can be 1, 2, 3, 4, 5, 6, 7, 8, 9, 10, 11, 12, 13, 14, 15, 16, 17, 18, 19, 20, 21, 22, 23, 24, 25 or more amino acids in length as long as the entire polypeptide comprising the isolated TNF-like PLAD is between 50 and 125 amino acid residues. R$_1$ and R$_2$ can also be the full or partial sequences of the TNF-like receptor that normally flank the TNF-like PLAD in a naturally occurring TNF-like receptor, wherein the polypeptide comprising the TNF-like PLAD is not the entire extracellular domain of a TNF-like receptor.

Further provided by this invention is a polypeptide of any size comprising the isolated amino acid sequence of a pre-ligand assembly domain (PLAD) of a TNF-like receptor, wherein the polypeptide is R$_1$-TNF-like receptor PLAD-R$_2$, wherein R$_1$ or R$_2$ comprise an amino acid sequence that does not flank the TNF-like receptor PLAD in a naturally occurring TNF-like receptor. R$_1$ or R$_2$, but not both can be fill or partial sequences of the TNF-like receptor that normally flank the TNF-like PLAD in a naturally occurring TNF-like receptor. For example, the PLAD can be from a TNF-like receptor and R$_1$ or R$_2$, can be amino acid sequences that are not present in the TNF-like receptor from which the TNF-like PLAD of the polypeptide was derived or any other TNF-like receptor. R$_1$ or R$_2$ can be any amino acid sequence as long as R$_1$-TNF-like PLAD-R$_2$ is not a naturally occurring TNF-like receptor. In another example, the PLAD can be from one TNF-like receptor and R$_1$ or R$_2$ or both, if present, can be peptide sequences from another TNF-like receptor. Therefore, one skilled in the art can combine the PLAD of one TNF-like receptor with R$_1$ or R$_2$ sequences from a different TNF-like receptor to obtain this polypeptide. Since the sequences of known TNF-like receptors are publicly available, the structure of R$_1$ and R$_2$ of the present polypeptide are numerous but well known and contemplated herein. Alternatively, R$_1$ or R$_2$ can be peptide sequences that are not related to any of the TNF-like receptor sequences.

Examples of polypeptides comprising the above-mentioned subsequence include: R$_1$-amino acids 1–54 of p60-R$_2$ (SEQ ID NO: 1); R$_1$-amino acids 10–54 of p80-R$_2$ (SEQ ID NO: 2); R$_1$-amino acids 1–43 of Fas-R$_2$ (SEQ ID NO: 3); R$_1$-amino acids 1–66 of Fas-R$_2$ (SEQ ID NO: 4); R$_1$-amino acids 13–50 of LtβR-R$_2$ (SEQ ID NO: 5); R$_1$-amino acids 6–39 of CD40-R$_2$ (SEQ ID NO: 6); R$_1$-amino acids 11–51 of CD30-R$_2$ (SEQ ID NO: 7); R$_1$-amino acids 742 of CD27-R$_2$ (SEQ ID NO: 8), R-amino acids 6–37 of HVEM-R$_2$ (SEQ ID NO: 9); R$_1$-amino acids 3–36 of OX40-R$_2$ (SEQ ID NO: 10), and R$_1$-amino acids 109–138 of DR4-R$_2$ (SEQ ID NO: 11).

As used herein an "isolated amino acid sequence of a PLAD" means a sequence which is substantially free from the naturally occurring materials with which the amino acid sequence is normally associated in nature. The polypeptides of this invention can comprise the entire amino acid sequence of a PLAD domain or fragments thereof. The polypeptides or fragments thereof of the present invention can be obtained by isolation and purification of the polypeptides from cells where they are produced naturally or by expression of exogenous nucleic acid encoding a PLAD. Fragments of a PLAD can be obtained by chemical synthesis of peptides, by proteolytic cleavage of the PLAD or the polypeptide comprising a PLAD and by synthesis from nucleic acid encoding the portion of interest. The PLAD may include conservative substitutions where a naturally occurring amino acid is replaced by one having similar properties. Such conservative substitutions do not alter the function of the polypeptide.

Thus, it is understood that, where desired, modifications and changes may be made in the nucleic acid encoding the polypeptides of this invention and/or amino acid sequence of the polypeptides of the present invention and still obtain a polypeptide having like or otherwise desirable characteristics. Such changes may occur in natural isolates or may be synthetically introduced using site-specific mutagenesis, the procedures for which, such as mis-match polymerase chain reaction (PCR), are well known in the art.

For example, certain amino acids may be substituted for other amino acids in a polypeptide without appreciable loss of functional activity. It is thus contemplated that various changes may be made in the amino acid sequence of the PLAD (or underlying nucleic acid sequence) without appreciable loss of biological utility or activity and possibly with an increase in such utility or activity. For example, the Q24A mutation, the D49R mutation and the K19E mutation in the natural sequence of p60 TNFR do not impair PLAD self-association.

These polypeptides can also be obtained in any of a number of procedures well known in the art. One method of producing a polypeptide is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to a particular protein can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a larger polypeptide. (Grant, ASynthetic Peptides: A User Guide, W. H. Freeman and Co., N.Y. (1992) and Bodansky and Trost, Ed., Principles of Peptide Synthesis, Springer-Verlag Inc., N.Y. (1993)). Alternatively, the peptide or polypeptide can be independently synthesized in vivo as described above. Once isolated, these independent peptides or polypeptides may be liked to form a larger protein via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al. Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. A Synthesis of Proteins by Native Chemical Ligation, Science, 266:776–779 (1994)). The first step is the chemoselective reaction of an unprotected synthetic peptide-%-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Clark-Lewis et al. FEBS Lett., 307:97 (1987), Clark-Lewis et al., J.Biol.Chem., 269:16075 (1994), Clark-Lewis et al. Biochemistry, 30:3128 (1991), and Rajarathnam et al. Biochemistry, 29:1689 (1994)).

Alternatively, unprotected peptide segments can be chemically linked where the bond formed between the peptide segments as a result of the chemical ligation is an unnatural (non-peptide) bond (Schnolzer et al. Science, 256:221 (1992)). This technique has been used to synthesize analogs of protein domains as well as large amounts of relatively pure proteins with full biological activity (deLisle Milton et al. A Techniques in Protein Chemistry IV, Academic Press, New York, pp. 257–267 (1992)).

The present invention also provides peptide mimetics for the disclosed polypeptides. A "peptide mimetic" is defined to include a chemical compound, or an organic molecule, or any other peptide mimetic, the structure of which is based on or derived from a binding region of a protein. For example, one can model predicted chemical structures to mimic the structure of a binding region, such as a PLAD. Such modeling can be performed using standard methods. Alternatively, peptide mimetics can also be selected from combinatorial chemical libraries in much the same way that peptides are. (Ostresh, J. M. et al., *Proc Natl Acad Sci USA* 1994; Nov. 8, 91(23):11138–42; Dorner, B. et al., *Bioorg Med Chem* 1996; May 4(5):709–15; Eichler, J. et al., *Med Res Rev* 1995; Nov. 15(6):481–96; Blondelle, S. E. et al. *Biochem J* 1, Jan. 1996; 313 (Pt 1):141–7; Perez-Paya, E. et al., *J Biol Chem* 23, Feb. 1996; 271(8):4120–6). Functional assays can also be utilized to select peptide mimetics.

The polypeptides of this invention can be linked to another moiety such as a nucleic acid, a protein, a peptide, a ligand, a carbohydrate moiety, viral proteins, a monoclonal antibody, a polyclonal antibody or a liposome. Furthermore, two or more PLAD containing polypeptides can also be linked to each other. For example, a bifunctional or multifunctional polypeptide containing two or more different PLADs can be made such that the polypeptide is capable of modulating the activity of more than one TNF-like receptor. The polypeptide can also contain two or more PLADs from the same TNF-like receptor in order to increase the avidity of this polypeptide for a particular TNF-like receptor.

Antibodies

Also provided by the present invention are antibodies that specifically bind to a PLAD of a TNF-like receptor. For example, the antibodies of the present invention can be antibodies that specifically bind to a PLAD of a TNF receptor, antibodies that specifically bind to a PLAD of FAS or antibodies that specifically bind a PLAD of DR4, to name a few. The antibody (either polyclonal or monoclonal) can be raised to any of the polypeptides provided and contemplated herein, both naturally occurring and recombinant polypeptides, and immunogenic fragments, thereof. The antibody can be used in techniques or procedures such as diagnostics, treatment, or vaccination. Anti-idiotypic antibodies and affinity matured antibodies are also considered.

Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al. *Bio/Technology*, 10:163–167 (1992); Bebbington et al. *Bio/Technology*, 10:169–175 (1992)). Humanized and chimeric antibodies are also comtemplated in this invention. Heterologous antibodies can be made by well known methods (See, for example, U.S. Pat. Nos. 5,545,806, 5,569,825, 5,625,126, 5,633,425, 5,661,016, 5,770,429, 5,789,650, and 5,814,318)

The phrase "specifically binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

Nucleic Acids

The present invention also provides nucleic acids that encode polypeptides of up to 125 amino acids comprising a PLAD of a TNF-like receptor as well as nucleic acids that encode polypeptides consisting of a TNF-like receptor PLAD.

The present invention also provides nucleic acids that encode a polypeptide of up to 125 amino acids comprising an isolated PLAD, wherein the polypeptide comprises the subsequence $R_1$-PLAD-$R_2$, wherein $R_1$ and $R_2$ are optional and when present can be H, acyl, $NH_2$, an amino acid or a peptide.

The invention further provides a nucleic acids that encodes a polypeptide comprising the isolated amino acid sequence of a pre-ligand assembly domain (PLAD) of a TNF-like receptor, wherein the polypeptide is $R_1$-TNF-like receptor PLAD-$R_2$, wherein $R_1$ or $R_2$ comprise an amino acid sequence that does not flank the TNF-like receptor PLAD in a naturally occurring TNF-like receptor.

As used herein, the term "nucleic acid" refers to single-or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the novel genes discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

A nucleic acid molecule encoding a PLAD can be isolated from the organism in which it is normally found. For example, a genomic DNA or cDNA library can be constructed and screened for the presence of the nucleic acid of interest. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989). Also contemplated by the present invention are nucleic acids encoding a PLAD that do not contain a ligand binding site.

Once the nucleic acid sequence of the desired PLAD is obtained, the sequence encoding specific amino acids can be modified or changed at any particular amino acid position by techniques well known in the art. For example, PCR primers can be designed which span the amino acid position or positions and which can substitute any amino acid for another amino acid. Then a nucleic acid can be amplified and inserted into the wild-type PLAD coding sequence in order to obtain any of a number of possible combinations of amino acids at any position of the PLAD. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423–462 (1985) and Zoller, M. J. "New molecular biology methods for protein engineering" Curr. Opin. Struct. Biol., 1:605–610 (1991). Techniques such as these can be used to alter the coding sequence without altering the amino acid sequence that is encoded.

Another example of a method of obtaining a DNA molecule encoding a PLAD is to synthesize a recombinant DNA molecule which encodes the PLAD. For example, oligonucleotide synthesis procedures are routine in the art and oligonucleotides coding for a particular protein region are readily obtainable through automated DNA synthesis.

A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al., "Receptor and Antibody Epitopes in Human Growth Hormone Identified by Homolog-Scanning Mutagenesis," Science, 243:1330–1336 (1989), have constructed a synthetic gene encoding the human growth hormone gene by first constructing overlapping and complementary synthetic oligonucleotides and ligating these fragments together. See also, Ferretti, et al., Proc. Nat. Acad. Sci. 82:599–603 (1986), wherein synthesis of a 1057 base pair synthetic bovine rhodopsin gene from synthetic oligonucleotides is disclosed. By constructing a PLAD in this manner, one skilled in the art can readily obtain any particular PLAD with desired amino acids at any particular position or positions within the PLAD. See also, U.S. Pat. No. 5,503,995 which describes an enzyme template reaction method of making synthetic genes. Techniques such as this are routine in the art and are well documented. These nucleic acids or fragments of a nucleic acid encoding a PLAD can then be expressed in vivo or in vitro as discussed below.

The nucleic acids encoding a polypeptide comprising or consisting of a PLAD can also be functionally linked to other nucleic acids to encode an immunoadhesin. For the purposes of the invention, the term "immunoadhesin" is defined as including any polypeptide encoded by a nucleic acid where at least a portion of a nucleic acid encoding a non-immunoglobulin molecule such as a PLAD is coupled to at least a portion of a nucleic acid encoding an immunoglobulin heavy chain polypeptide, IgG for example. The Fc regions of IgG2, IgG3, IgM, IgA, IgE can also be utilized to construct an immunoadhesin. The coupling may be achieved in a manner which provides for a functional transcribing and translating of the nucleic acid segment and message derived therefrom, respectively. These IgG immunoadhesins can be expressed by transient or stable transfection in a variety of mammalian host cells as well as in baculovirus-infected cells. Similar to antibodies, IgG immunoadhesins can be purified from the culture medium into which they are secreted by single-step protein A or protein G affinity chromatography.

The invention also provides for the isolated nucleic acids encoding a PLAD in a vector suitable for expressing the nucleic acid. Once a nucleic acid encoding a particular PLAD of interest, or a region of that nucleic acid, is constructed, modified, or isolated, that nucleic acid can then be cloned into an appropriate vector, which can direct the in vivo or in vitro synthesis of that wild-type and/or modified PLAD. The vector is contemplated to have the necessary functional elements that direct and regulate transcription of the inserted gene, or nucleic acid These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.).

There are numerous E. coli (Escherichia coli) expression vectors known to one of ordinary skill in the art which are useful for the expression of the nucleic acid insert. Other microbial hosts suitable for use include bacilli, such as Bacillus subtilis, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, et al., Alpha-Factor-Directed Synthesis and Secretion of Mature Foreign Proteins in *Saccharomyces cerevisiae*. Proc. Nat. Acad. Sci., 81:4642–4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, genticin or G418 resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other eukaryotic cellular hosts.

Alternative vectors for the expression of genes or nucleic acids in mammalian cells, those similar to those developed for the expression of human gamma-interferon, tissue plasminogen activator, clotting Factor VIII, hepatitis B virus surface antigen, protease Nexin1, and eosinophil major basic protein, can be employed. Further, the vector can include CMV promoter sequences and a polyadenylation signal available for expression of inserted nucleic acids in mammalian cells (such as COS-7).

Insect cells also permit the expression of mammalian proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographica californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion negative viruses which form plaques that are distinctively different from those of wild-type occlusion positive viruses. These distinctive plaque morphologies allow visual screening for recombinant viruses in which the AcNPV gene has been replaced with a hybrid gene of choice.

The invention also provides for the vectors containing the contemplated nucleic acids in a host suitable for expressing the nucleic acids. The vectors containing the nucleic acid segments of interest can be transferred into host cells by well-known methods, which vary depending on the type of cellular host. For example, calcium chloride transformation, transduction, and electroporation are commonly utilized for prokaryotic cells, whereas calcium phosphate, DEAE dextran, or lipofection mediated transfection or electroporation may be used for other cellular hosts.

Alternatively, the nucleic acids of the present invention can be operatively linked to one or more of the functional elements that direct and regulate transcription of the inserted nucleic acid and the nucleic acid can be expressed. For example, a nucleic acid can be operatively linked to a bacterial or phage promoter and used to direct the transcription of the nucleic acid in vitro. A further example includes using a nucleic acid provided herein in a coupled transcription-translation system where the nucleic acid directs transcription and the RNA thereby produced is used as a template for translation to produce a polypeptide. One skilled in the art will appreciate that the products of these reactions can be used in many applications such as using labeled RNAs as probes and using polypeptides to generate antibodies or in a procedure where the polypeptides are being administered to a cell or a subject.

Expression of the nucleic acid, in combination with a vector, can be by either in vivo or in vitro. In vivo synthesis comprises transforming prokaryotic or eukaryotic cells that can serve as host cells for the vector. Alternatively, expression of the nucleic acid can occur in an in vitro expression system. For example, in vitro transcription systems are commercially available which are routinely used to synthesize relatively large amounts of mRNA. In such in vitro transcription systems, the nucleic acid encoding a PLAD would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired PLAD polypeptide. (Stratagene Cloning Systems, La Jolla, Calif.).

Gene Therapy Methods

Using gene therapy methods, a nucleic acid encoding a polypeptide comprising or consisting of a PLAD can be administered. The nucleic acid encoding the polypeptide of this invention can be placed into a vector and delivered to the cells of a subject either in vivo or ex vivo by standard methods.

The nucleic acid encoding the polypeptide of this invention may be functionally attached to a specific leader peptide which can specify for secretion of the polypeptide. For example the polypeptide can have a signal sequence, such as the the murine Ig-kappa signal sequence (Blezinger et al. Nat. Biotechnol. 17: 343–8, 1999), rat insulin leader sequence (Fakhral et al. J. Immunother. 20: 437–8, 1997), FGF-4 signal sequence (Ueno et al. Ateriloscler. Thromb. Vase. Biol., 17: 2453–2460, 1997), human growth hormone signal peptide (Rade et al. Gene Ther. 6: 385–92, 1999), beta lactamase signal sequence (Hughes et al. Hum. Gene Ther. 5: 1445–55, 1994), bovine prolactin signal sequence (Gorman et al. Bran Res. Mol. Brain Res. 44:143–146, 1997) and other similar signal sequences.

For in vivo administration, the cells can be in a subject and the nucleic acid can be administered in a pharmaceutically acceptable carrier. The subject can be any animal in which it is desirable to selectively express a nucleic acid in a cell. In a preferred embodiment, the animal of the present invention is a human. In addition, non-human animals which can be treated by the method of this invention can include, but are not limited to, cats, dogs, birds, horses, cows, goats, sheep, guinea pigs, hamsters, gerbils and rabbits, as well as any other animal in which selective expression of a nucleic acid in a cell can be carried out according to the methods described herein.

In the method described above which includes the introduction of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid inside the cell. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a Sonoporation machine (ImaRx Pharmaceutical Corp., Tucson, Ariz.).

As one example, vector delivery can be via a viral system, such as a retroviral vector system which can package a recombinant retroviral genome. The recombinant retrovirus can then be used to infect and thereby deliver nucleic acid to the infected cells. The exact method of introducing the nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors, and pox virus vectors, such as vaccinia virus vectors. Physical transduction techniques can also be used, such as liposome delivery and receptor-mediated and other endocytosis mechanism. This invention can be used in conjunction with any of these or other commonly used gene transfer methods.

The nucleic acid and the nucleic acid delivery vehicles of this invention, (e.g., viruses; liposomes, plasmids, vectors) can be in a pharmaceutically acceptable carrier for in vivo administration to a subject. By "pharmaceutically acceptable" is meant a material that is not biologically or otherwise undesirable, i.e., the material may be administered to a subject, along with the nucleic acid or vehicle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The nucleic acid or vehicle may be administered orally, parenterally (e.g., intravenously), by intramuscular injection, by intraperitoneal injection, transdermally, extracorporeally, topically or the like. The exact amount of the nucleic acid or vector required will vary from subject to subject, depending on the species, age, weight and general condition of the subject, the severity or mechanism of any disorder being treated, the particular nucleic acid or vehicle used, its mode of administration and the like.

Inhibitors of PLAD Self-Association

The present invention further provides a composition comprising an inhibitor of PLAD self-association or TNF-like receptor oligomerization. An "inhibitor" is defined as a compound that binds a PLAD or a compound, including antibodies, that binds the target for a PLAD and prevents an activity of a PLAD. Upon binding to a PLAD, the inhibitor can disrupt or prevent PLAD self-association, thus inhibiting TNF-like receptor oligomerization. The inhibitor of TNF-like receptor oligomerization can be an antibody, either polyclonal or monoclonal, that specifically binds to a PLAD, a ligand that binds to a PLAD, a polypeptide that binds to a PLAD, a compound that binds to a PLAD or a peptide mimetic based on a PLAD. For example, a polypeptide comprising or consisting of a PLAD can associate with the PLAD of a naturally occurring TNF-like receptor, thus preventing or inhibiting the TNF-like receptor from self-associating with other naturally occurring TNF-like receptors. Anti-idiotypic antibodies and affinity matured antibodies are also considered. Other inhibitors include, but are not limited to molecules or compounds designed to block PLAD self-association. The inhibitor can be a whole protein or a fragment of a protein that inhibits PLAD self-association, thus preventing TNF-like receptor oligomerization. Crystal structures of the TNF receptors and their oligomeric complexes may be utilized to design molecules that may disrupt PLAD self-association. The crystal structures can also be analyzed to design molecules that mimic PLAD and disrupt PLAD self-association. The invention also contemplates targeting other regions of TNF-like receptors such that upon binding that region, the conformation of a PLAD in the receptor is disrupted thus preventing it from associating with another PLAD. For example, one skilled in the art could target the CRD3 of p60 TNFR, such that upon binding the CRD3 region of p60 TNFR, the conformation of the receptor is changed, thus preventing the PLAD of the p60 TNFR from associating with another PLAD.

Thus, further provided by the present invention is a method of inhibiting TNF-like receptor oligomerization in a cell by administering an effective amount of an inhibitor of TNF-like receptor oligomerization.

The invention also contemplates enhancing PLAD self-association in order to enhance the effects of a TNF-like receptor. For example, there are circumstances in which it would be desirous to enhance TNFR signaling. In such instances, agonists of PLAD self association, such as certain antibodies or molecules that bind to a PLAD and have the specific property of enhancing PLAD self association, can be utilized to convert cells that are resistant to TNFR effects due to weak PLAD interactions, into cells that are responsive to TNFR effects. Such enhanced PLAD self association can increase ligand binding as well as signaling. Examples of disease states where such enhanced PLAD interactions would be desirable include, but are not limited to, autoimmune lymphoproliferative syndrome (ALPS) and hyper IgM syndrome.

The invention also provides for utilizing a PLAD as a targeting moiety to deliver biological agents to cells. For example, a PLAD linked to a toxin can be delivered to cells, such that upon binding to a naturally occuring PLAD on a TNF-R, oligomerization is inhibited and upon internalization of the naturally occurring TNF-R, the PLAD linked to the toxin is internalized as well, thus delivering the toxin to the cell.

As used throughout, "TNF-like receptor" refers to any member of the TNF receptor superfamily that includes, but is not limited to: TNF-R, p60 (also known as p55 and TNFR1), p80 (also known as p75, TNFR2), Fas (CD95/APO-1), TRAIL receptor, LTβR, CD40, CD30, CD27, HVEM, OX40, DR4, TROY, EDAR, XEDAR, DCR3, AITR, 4-1BB, DR3, RANK, TACI, BCMA, DR6, DPG, DR5, DCR1 AND DCR2 (See Table 1).

As previously stated, inhibitors of TNF oligomerization include antibodies, ligands, peptide mimetics, compounds and polypeptides that specifically bind to a PLAD. These polypeptides include polypeptides comprising or consisting of an isolated PLAD.

The present invention also provides a method of inhibiting ligand binding to a TNF-like receptor by administering an effective amount of an inhibitor of TNF-like receptor oligomerization. For example, by administering an inhibitor, such as a polypeptide comprising or consisting of a TNFR-PLAD, TNF receptor oligomerization would be inhibited, thus preventing the binding of TNF-α to the TNF receptor and diminishing the deleterious effects of TNF-α. Similarly, the administration of a polyeptide comprising a CD40 receptor-PLAD (CD40R-PLAD), would inhibit CD40R oligomerization, thus preventing the binding of CD40 ligand to the CD40R and diminishing the deleterious effects of CD40 in disease states such as allograft rejection, rheumatoid athritis and systemic lupus erythematosis. Inhibition of ligand binding to a TNF-like receptor results in inhibition of signal transduction via TNF-like receptors, thus providing a method of modulating signaling via TNF-like receptors. Furthermore, the present invention has established that TNF-like receptors bind ligand and signal via homotypic association, i.e. TNFR-PLAD interacts with TNFR-PLAD; Fas-PLAD interacts with Fas-PLAD; CD40-PLAD interacts with CD40-PLAD etc. Therefore, therapy with PLAD self-association disrupting peptides and peptide mimetics would ensure receptor specific therapy because the present invention shows that each receptor associates only with itself through the PLAD. For example, disrupting TNF-R1 function without affecting TNF-R2 may have major benefits above current non-selective therapeutics. Similarly, the specific disruption of a particular TNF-like receptor function without affecting other TNF-like receptor functions is highly desirable.

Protein Therapy Methods

The present invention also provides a method of treating inflammation in a subject by administering an effective amount of an inhibitor of PLAD self-association.

The present invention also provides a method of treating inflammation associated with an autoimmune disease in a subject by administering an effective amount of an inhibitor of PLAD self-association. Such diseases include, but are not limited to, periodic fever syndromes, sepsis syndromes and adult respiratory distress syndrome.

In the present invention, the subject can be any mammal, preferably human, and can include but is not limited to mouse, rat, guinea pig, hamster, rabbit, cat, dog, goat, monkey, horse and chimpanzee.

As used herein, "treating" describes an improvement in the patient's clinical state. The improvement may range from reduction of the inflammatory response to complete amelioration of the inflammatory disease.

As used herein, "autoimmune disease" describes a disease state or syndrome whereby a subject's body produces a dysfunctional immune response against the subject's own body components, with adverse effects. This may include production of B cells which produce antibodies with specificity for all antigens, allergens or major histocompatibility (MHC) antigens, or it may include production of T cells bearing receptors that recognize self-components and produce cytokines that cause inflammation. Examples of autoimmune diseases include, but are not limited to, ulcerative colitis, Crohn's disease, multiple sclerosis, rheumatoid arthritis, diabetes mellitus, pernicious anemia, autoimmune gastritis, psoriasis, Bechet's disease, Wegener's granulomatosis, Sarcoidois, autoimmune thyroiditis, autoimmune oophoritis, bullous pemphigoid, phemphigus, polyendocrinopathies, Still's disease, Lambert-Eaton myasthenia syndrome, myasthenia gravis, Goodpasture's syndrome, autoimmune orchitis, autoimmune uveitis, systemic lupus erythematosus, Sjogren's Syndrome and ankylosing spondylitis.

Since certain TNFR receptors, such as HVEA, are viral receptors, and these receptors may depend on oligomerization, the present invention also contemplates blocking viral entry by preventing PLAD assembly.

Optimal dosages used will vary according to the individual being treated and the inhibitor being used. The amount of inhibitor will also vary among individuals on the basis of age, size, weight, condition, etc. One skilled in the art will realize that dosages are best optimized by the practicing physician and methods for determining dose amounts and regimens and preparing dosage forms are described, for example, in *Remington's Pharmaceutical Sciences*. For example, suitable doses and dosage regimens can be determined by comparison to agents presently used in the treatment or prevention of inflammation or autoimmune disorders.

Typically, the inhibitor of this invention can be administered orally or parenterally in a dosage range of 0.1 to 100 mg/kg of body weight depending on the clinical response that is to be obtained. Administration of inhibitor can be stopped completely following a prolonged remission or stabilization of disease signs and symptoms and readministered following a worsening of either the signs or symptoms of the disease, or following a significant change in immune status, as determined by routine follow-up immunological studies well known to a clinician in this field.

The efficacy of administration of a particular dose of inhibitor in treating inflammation or an autoimmune disorder as described herein can be determined by evaluating the particular aspects of the medical history, the signs, symptoms and objective laboratory tests that have a documented utility in evaluating pathophysiological activity of the particular disorder being treated. These signs, symptoms and objective laboratory tests will vary depending on the particular disorder being treated, as will be well known to any clinician in this field. For example, if, based on a comparison with an appropriate control group and knowledge of the normal progression of the disorder in the general population or the particular individual, 1) a subject's frequency or severity of recurrences is shown to be improved; 2) the progression of the disease or disorder is shown to be stabilized; or 3) the need for use of other immunosuppressive medications is lessened, then a particular treatment can be considered efficacious.

Once it is established that disease activity is significantly improved or stabilized by a particular inhibitor, specific signs, symptoms and laboratory tests can be evaluated in accordance with a reduced or discontinued treatment schedule. If a disease activity recurs, based on standard methods of evaluation of the particular signs, symptoms and objective laboratory tests as described herein, treatment can be reinitiated.

Additionally, the efficacy of administration of a particular dose of a peptide ligand in preventing an autoimmune disorder in a subject not known to have an autoimmune disorder, but known to be at risk of developing an autoimmune disorder, can be determined by evaluating standard signs, symptoms and objective laboratory tests, known to one of skill in the art, over time. This time interval may be long (i.e., years/decades). The determination of who would be at risk for the development of an autoimmune disorder would be made based on current knowledge of the known risk factors for a particular disorder familiar to clinicians and researchers in this field, such as a particularly strong family history of a disorder or exposure to or acquisition of factors or conditions which are likely to lead to development of an autoimmune disorder.

By "pharmaceutically acceptable" is meant a material that is not biologically or otherwise undesirable, i.e., the material may be administered to an individual along with the selected compound without causing any undesirable biological effects or interacting in a undesirable manner with any of the other components of the pharmaceutical composition in which it is contained. The carrier may depend on the method of administration and the particular patient. Methods of administration can be oral, sublingual, mucosal, inhaled, absorbed, or by injection. It is also noted that not all methods of administering the inhibitors of TNF-like receptor oligomerization described herein require a pharmaceutically acceptable carrier.

In the present invention, the inhibitors of PLAD self-association or TNF-like oligomerization can be orally or parenterally administered in a carrier pharmaceutically acceptable to human subjects. Suitable carriers for oral or inhaled administration can include one or more of the carriers pharmaceutically acceptable to human subjects. Suitable carriers for oral administration include one or more substances which may also act as a flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pyrogen free saline, pharmaceutically accepted oils, or a mixture of any of these. The liquid can also contain other suitable pharmaceutical addition such as buffers, preservatives, flavoring agents, viscosity or osmoregulators, stabilizers or suspending agents. Examples of suitable liquid carriers include water with or without various additives, including carboxypolymethylene as a ph-regulated gel. The inhibitor may be contained in enteric coated capsules that release the polypeptide into the intestine to avoid gastric breakdown. For parenteral administration of the antagonist, a sterile solution or suspension is prepared in saline that may contain additives, such as ethyl oleate or isopropyl myristate, and can be injected for example, into subcutaneous or intramuscular tissues, as well as intravenously.

Screening Methods

A method of screening for an inhibitor of PLAD association comprising: a) transfecting a cell with a plasmid containing a nucleic acid comprising a nucleic acid sequence encoding an isolated PLAD and a plasmid comprising a nucleic acid sequence encoding a second isolated PLAD; b) contacting the cell with a putative inhibitor and; c) measuring PLAD self association, wherein a decrease in PLAD association in the cell of step b) as compared to PLAD association in a cell that was not contacted with the putative inhibitor indicates the presence of an inhibitor of PLAD-association.

One example of this screening method is a method of screening for an inhibitor of PLAD-association comprising: a) transfecting a cell with a plasmid containing a nucleic acid comprising a nucleic acid sequence encoding an isolated PLAD functionally linked to a flourescence donor and a plasmid comprising a nucleic acid sequence encoding an isolated PLAD functionally linked to a flourescence donor; b) contacting the cell with the inhibitor; and c) measuring FRET, wherein a decrease in FRET as compared to FRET measurement in a cell that was not contacted with the inhibitor indicates the presence of an inhibitor of PLAD-association.

Also provided by the present invention is a method of screening for an agonist of PLAD association comprising: a) transfecting a cell with a plasmid containing a nucleic acid comprising a nucleic acid sequence encoding an isolated PLAD and a plasmid comprising a nucleic acid sequence encoding a second isolated PLAD; b) contacting the cell with a putative agonist and; c) measuring PLAD self association, wherein an increase in PLAD association in the cell of step b) as compared to PLAD association in a cell that was not contacted with the putative agonist indicates the presence of an agonist of PLAD-association.

The Examples below exemplify the use of FRET to measure PLAD association. Furthermore, in performing the screening methods described above, a single plasmid can be utilized to deliver more than one nucleic acid encoding a PLAD. In methods involving FRET analysis, a single plasmid can be utilized to deliver more than one nucleic acid encoding a PLAD functionally linked to a fluorescence donor or acceptor.

One skilled in the art could also utilize a yeast two hybrid screening method to screen for inhibitors or agonists of PLAD association. Inhibitors or agonists of PLAD association can also be identified by utilizing cellular assays which can include, but are not limited to, apoptosis induction, NF-KB induction, lymphocyte maturation or activation, and necrosis induction (3, 4, 8, 15, 29, 33, 42, 45).

The present invention is more particularly described in the following examples which are intended as illustrative only since numerous modifications and variations therein will be apparent to those skilled in the art.

EXAMPLE I

H9 lymphoma cells were washed and resuspended in PBS. The cells were then incubated with 100 ng/ml of human recombinant TNFα (R&D Systems) for 1 hour at 4° C. with rotation. Cells were then treated with 2 mM of the crosslinker DTSSP (Pierce) for 30 minutes and the reaction was quenched with 20 mM Tris.Cl [pH 7.5] for 15 minutes on ice. The cells were lysed in 150 mM NaCl, 20 mM Tris.Cl [pH 7.5], 1 mM EDTA, 30 mM NaF, 2 mM b-glycerophosphate and 1 mM sodium orthovanadate with protease inhibitors added (Boehringer Mannheim). Equal amounts of the lysates were subjected to electrophoresis under non-reducing (without β-mercaptoethanol) or reducing (with 280 mM β-mercaptoethanol) conditions and analyzed for p60 and p80 complexes with specific antibodies (19). Densitometry was performed with a Kodak Image Station 440.

Complexes were found for p80 that exhibited molecular sizes approximately three times the unit size, consistent with glycosylated and non-glycosylated trimers (FIG. 1A). Surprisingly, p80 complexes were efficiently captured in the presence or absence of TNFα (65–70% of chains by densitometry, FIG. 1A, lanes 3 and 4). Despite the fact that most p60 resides in the Golgi apparatus and was inaccessible to the crosslinker (7), as much as 15–20% of the p60 chains were cross-linked as apparent trimers and discrete higher order complexes, whether or not TNFα was added (FIG. 1A, lanes 11 and 12). Control experiments revealed no detectable endogenous TNFα and no evidence of other proteins such as p80 crosslinked to the p60 complex. Western blot analysis confirmed the absence of TNFα in the lysates. Immunoprecipitation of the crosslinked complexes with anti-p60 antibody revealed no detectable level of p80 in the p60 complex in Western blots.

The complexes were resolved into monomers by cleaving the crosslinker with β-mercaptoethanol (FIG. 1A, lanes 7, 8, 15 and 16). Thus, these results are suggestive of p60 and p80 chain self-association prior to ligand binding.

To validate the possibility of ligand-independent self-assembly, a domain in the TNFR that would mediate this phenomenon was identified. It is well established that the cytoplasmic death domain of p60 can self-associate and trigger apoptosis when over-expressed (8). However, since the pre-assembled complexes observed were apparently non-signaling, it was hypothesized that the assembly domain resides outside of the cytoplasmic region. It was found that the N-terminal regions of the ECDs of p60 and p80 could specifically self-associate in a yeast two-hybrid interaction assay (9).

The various truncations and mutations of p60, p80, HVEM, DR4 and CD40 were generated by Polymerase chain reaction (PCR) and sequenced. Briefly, the leader sequence and the first ten amino acid residues from p80 was amplified so that the HA epitope tag was included at the 3' end to create a HA tag at the N-terminus of the receptors. The PCR product was digested with BamHI and EcoRI and cloned into pcDNA3. The PCR fragments containing the receptor fragments were then introduced into this plasmid using the EcoRI and XhoI sites. For the GFP/CFP/YFP chimeras, the fragments were amplified by PCR and introduced in-frame into the XhoI and XbaI sites of p60ΔCD-HA. 293T cells were transfected with Fugene 6 (Boehringer Mannheim) as per manufacturer's protocol. Cells were lysed in 150 mM NaCl, 20 mM Tris.Cl [pH 7.5], 1 mM EDTA, 30 mM NaF, 2 mM β-glycerophosphate, 1 mM sodium orthovanadate, 5 mM iodoacetamide, 2 mM dithiothreitol (DTT), 1% TRITON X-100 and protease inhibitors (Boehringer Mannheim). After pre-clearing with protein G agarose beads (Boehringer Mannheim) and normal mouse IgG, proteins were immunoprecipitated from the lysates with 2 mg anti-GFP and protein G agarose beads. Immune complexes were washed twice with lysis buffer containing 0.5 M NaCl and then three times with regular lysis buffer. Immune-complexes were resolved on Tris/Glycine gels (Novex). Transfection in Jurkat cells showed similar results. In mammalian cells, it was found that a chimeric p60 receptor with the cytoplasmic domain replaced by the green fluorescent protein (GFP) interacted strongly with a tailless p60 (p60ΔCD-HA) but not with the TNFR-like receptor herpesvirus entry mediator (HVEMΔCD-HA) (FIG. 1B, compare lanes 2 and 3).

Figure 1B:
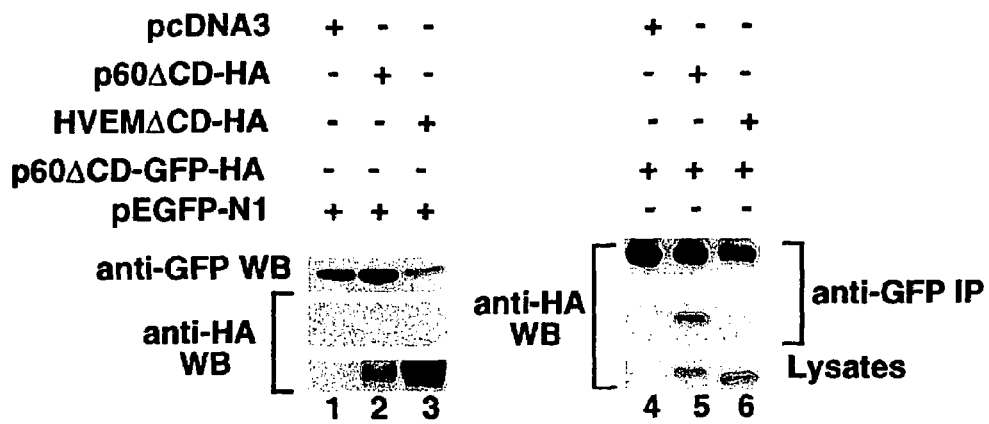
FIG. 1B illustrates specific p60 TNFR self-association. 293T cells were transfected with p60ΔCD-GFP-HA (lanes 1–3) or pEGFP-N1 (lanes 4–6) and either pcDNA3 (lanes 1, 4), p60ΔCD-HA (lanes 2, 5) or HVEMΔCD-HA (lanes 3, 6). Immunoprecipitation was carried out with anti-GFP antibody (GFP IP in the top 2 panels) and blotted with anti-HA antibody (HA WB) or anti-GFP antibody (GFP WB) as indicated. The top and middle panels show the precipitated p60ΔCD-GFP-HA (or GFP) and p60ΔCD-HA respectively. The bottom panels show the p60ΔCD-HA and HVEMΔCD-HA proteins in cell lysates. Results represent five experiments.

GFP alone failed to associate with p60ΔCD-HA (FIG. 1B, lane 5). A similar homotypic interaction of the extracellular portion was observed between full-length p80 and a tailless p80 (FIG. 1C, lane 6).

Figure 1C:
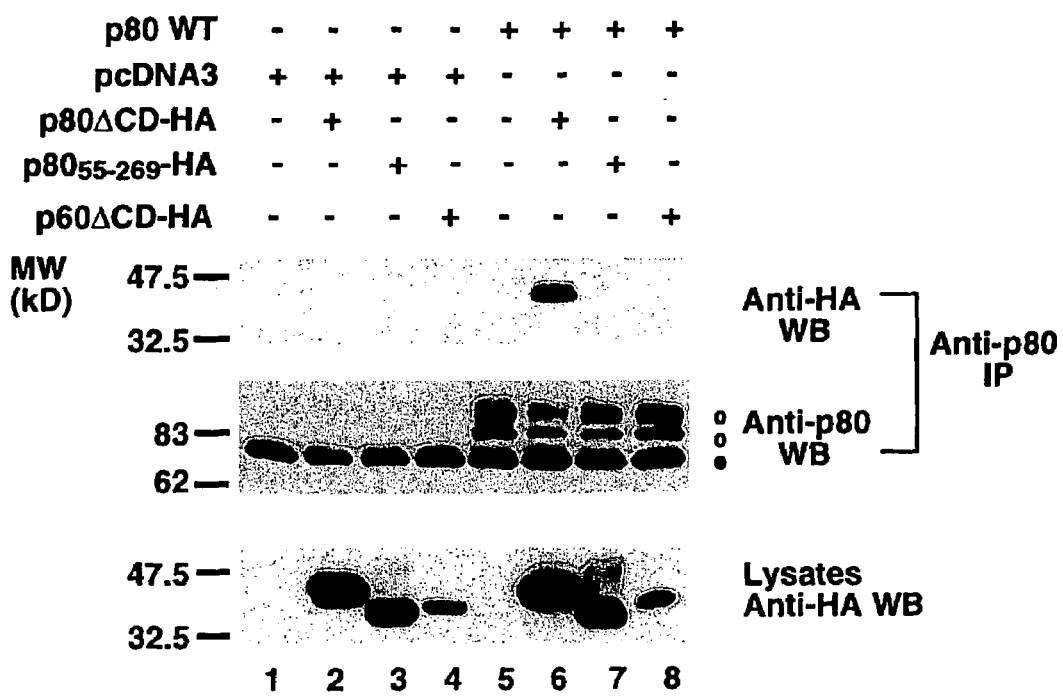
FIG. 1C illustrates specific p80 self-association and the definition of the Pre-Ligand Assembly Domain (PLAD). 293T cells were transfected with the plasmids indicated at the top. Immunoprecipitation was performed with a C-terminal-specific anti-p80 antibody (p80 IP) that recognizes only the full-length p80 (top and middle panels). The expression of the truncated p80 or p60 proteins in the lysates is shown in the bottom panel. Western blots were performed with anti-HA antibody (top and bottom panels) and the C-terminal specific anti-p80 antibody (middle panel). The open circles represent the glycosylated and unglycosylated forms of p80. The closed circle denotes the Ig heavy chain.

Moreover, removal of as little as amino acids (a.a)10–54 of p80, overlapping CRD1, completely abrogated ligand-independent association with intact p80 (FIG. 1C, lane 7). Self-association was eliminated by a similar deletion (a.a.1–54) in p60 (see below).

Figure 1D:
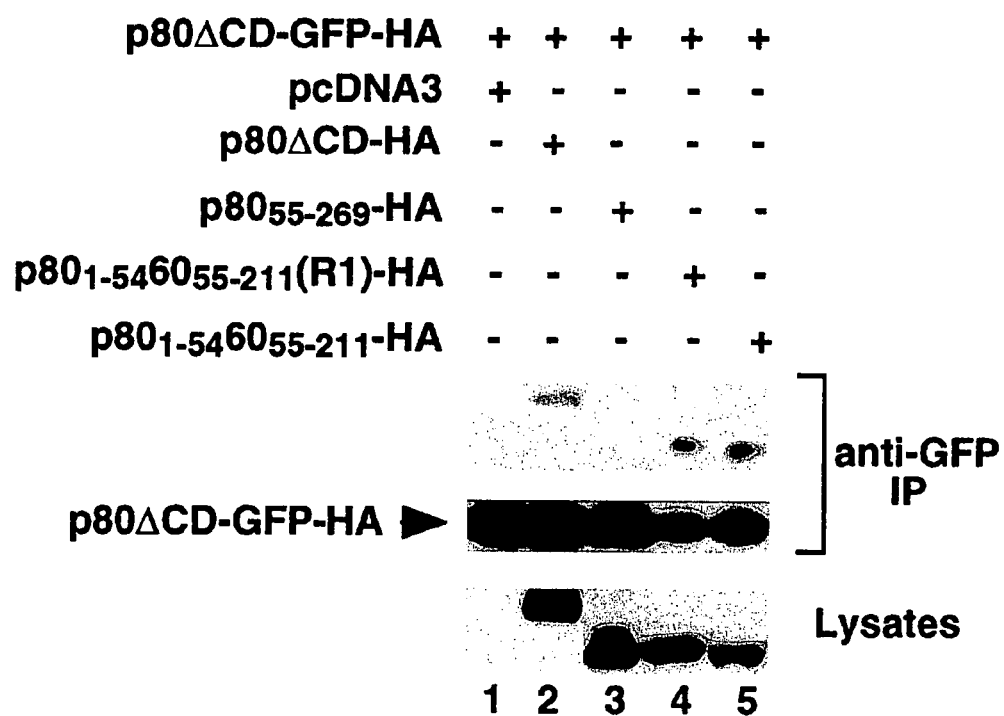
FIG. 1D illustrates that PLAD is sufficient for receptor self-association. 293T cells were transfected with p80ΔCD-GFP-HA (lanes 1–5) together with the plasmids indicated at the top of each lane. Immunoprecipitation was performed with anti-GFP antibody and Western blots with anti-HA antibody. The co-precipitated DCD proteins and their expression in total cell lysates are shown in the middle and bottom panels respectively. The top panel shows the precipitated p60ΔCD-GFP-HA protein.
Figure 1E:
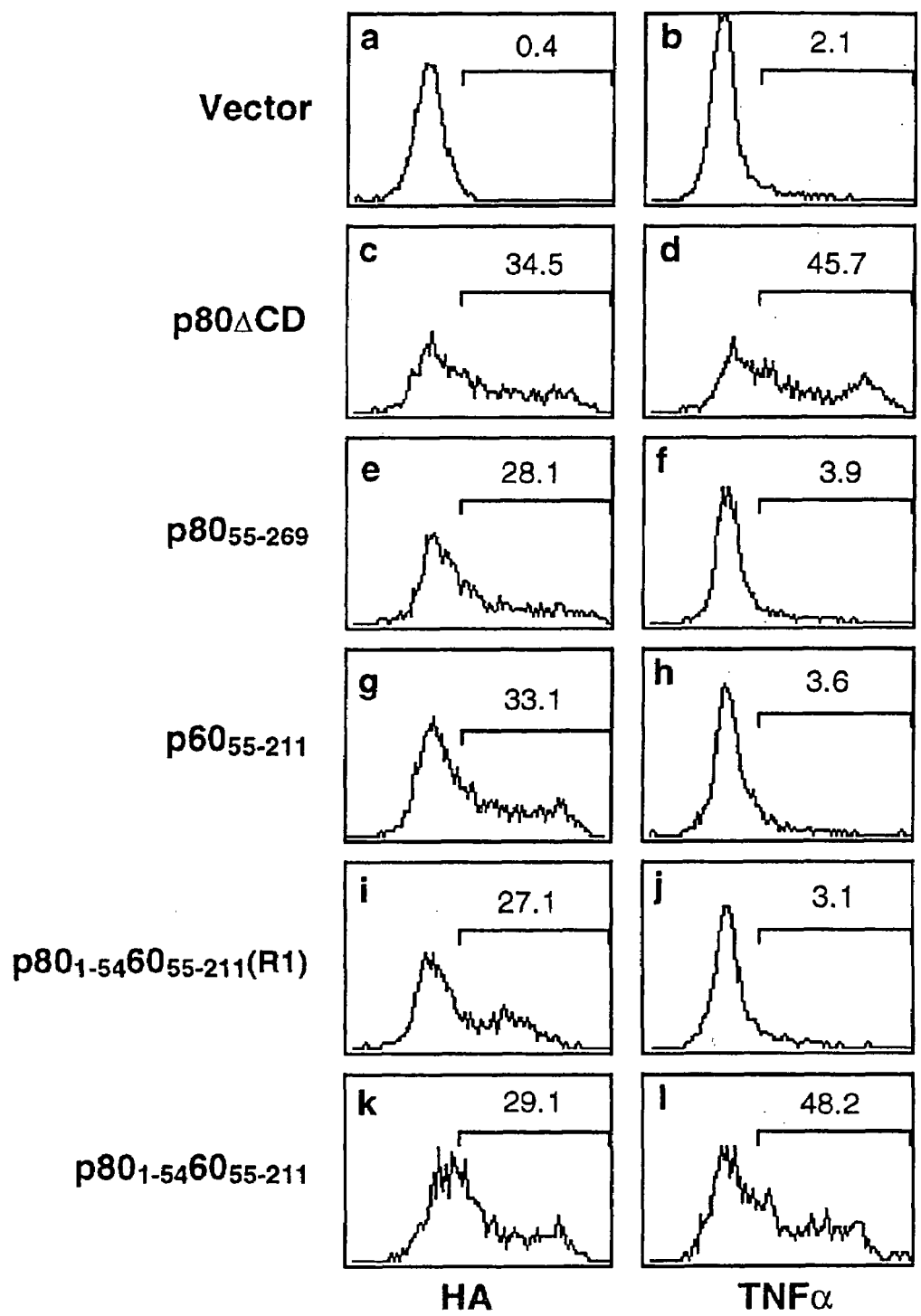
FIG. 1E illustrates the PLAD is essential for TNFα binding. Histograms show the expression of transfected receptors (by anti-HA staining) and their binding to TNFα in 293T cells transfected with the indicated constructs (25). The x-axis shows the intensity of fluorescence and the y-axis shows the cell number. The numbers shown are percentages of positive population compared to the vector-transfected control.
Figure 9:
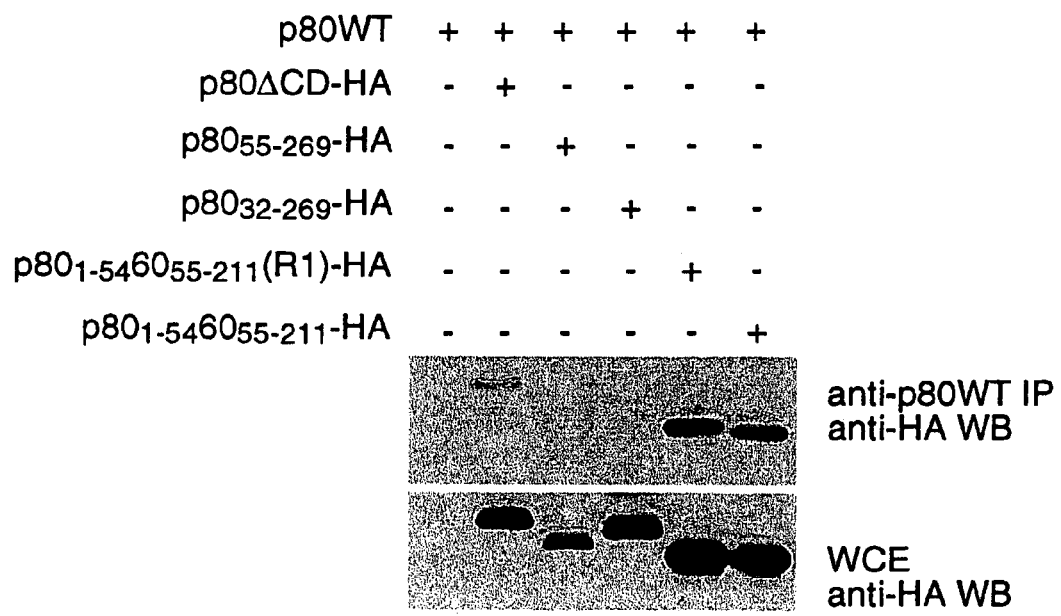
FIG. 9 shows the analysis of immunoprecipitates for the presence of p80 chimeric receptors or truncations. 293T cells were transfected with the indicated plasmids and harvested for co-immunoprecipitation using an anti-p80 COOH-terminal specific antibody. The immunoprecipitates were analyzed for the presence of p80 chimeric receptors or truncations using anti-HA antibody in Western blot analysis (top panel). The bottom panel shows the expression of the HA-tagged proteins in whole cell lysates.

The importance of the N-terminal portion of p80 (a.a.10–54) is further illustrated by appending it to the p60 receptor which then interacted with full-length p80 (FIG. 1D, compare lane 3 to lanes 4 and 5, FIG. 9). Thus, this domain was sufficient to mediate specific association of a heterologous receptor. This association is ligand-independent because the chimera $p80_{10-54}60_{55-211}$(R1) has two amino acids encoded by an EcoRI restriction site inserted at the junction of the p80 and p60 sequences that abolished TNFα binding (FIG. 1E, panels k and l). Thus, a novel functional domain distinct from the ligand-binding pocket of the TNFR-ECD mediates self-assembly in the absence of ligand. Henceforth, this domain is referred to as the Pre-Ligand Assembly Domain (PLAD).

Figure 2A:
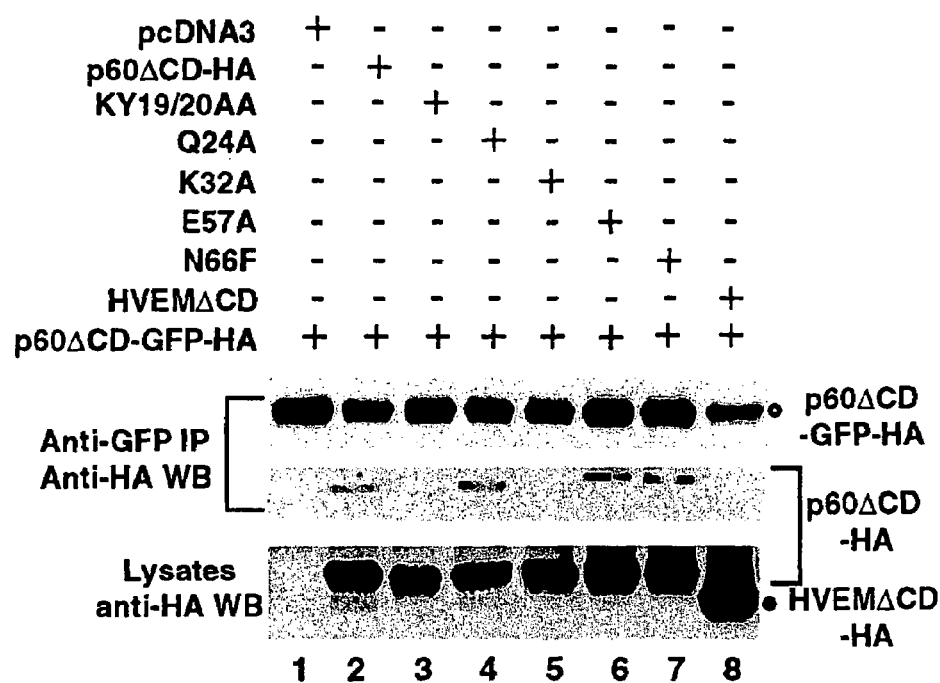
FIG. 2A illustrates that replacement of residues in the PLAD prevents self-association. 293T cells were transfected with the indicated plasmids. Immunoprecipitation was performed as in FIG. 1 with anti-GFP antibody. Western blots were performed with anti-HA antibody. The top and middle panels show the precipitated p60ΔCD-GFP-HA (open circle) and p60ΔCD-HA mutant proteins (bracket) respectively. The bottom panel shows the expression of p60ΔCD-HA mutants (bracket) and HVEMΔCD-HA (filled circle) in cell lysates.

The deletion of the PLAD from either p60 or p80 completely abrogated ligand binding (Table 2 and FIG. 1E, compare panels d, f, and h). However, addition of the PLAD from p80 enabled the PLAD-deleted p60 to bind TNFα but, as indicated above, this was abolished by the two amino acids insertion encoded by an EcoRI site (FIG. 1E, panels j and l). Thus, efficient TNFα binding by TNFRs could depend on receptor self-assembly. Alternatively, removal of the PLAD may have disrupted the overall ECD structure. The latter possibility is unlikely as previous results showed that removal of CRD1 does not disrupt proper folding of the p60 ECD (13). To definitively distinguish these possibilities, however, amino acid substitutions into CRD1-3 of p60ΔCD-HA were introduced and their effect on interaction with p60ΔCD-GFP-HA was determined. Mutagenesis was performed using the Quikchange method (Stratagene) as per manufacturer's instructions. The mutations were confirmed by DNA sequencing. All amino acids replaced except K19 are conserved between p60 and p80. The corresponding residue in p80 is E22. Two substitutions in the PLAD that are not expected to disturb direct ligand contact, KY19/20AA and K32A (5), abrogated self-association (FIG. 2A, compare lanes 3 and 5 to lane 2) and eliminated TNFα binding (Table 2). Substitution of another residue within the PLAD, Q24A, did not affect self-association or TNFα binding (FIG. 2A, lane 4 and Table 2). Two other substitutions outside of the PLAD in the CRD2 ligand binding pocket, E57A and N66F, disrupted TNFα binding but had little effect on receptor self-association (Table 2 and FIG. 2A, lanes 6 and 7). It was also found that the association of a mutant receptor lacking the cytoplasmic tail with the wild type ECD correlates with its ability to dominantly interfere with p60-induced apoptosis, indicating that the mutant receptors enter into endogenous functional p60 receptor complexes via the PLAD (Table 2). These results show that the PLAD is physically distinct from the ligand contact domain but is nonetheless essential for efficient TNFα binding and receptor function.

Unlike monomeric receptor chains, the cytoplasmic portions of the receptor chains within a pre-assembled receptor complex might be expected to be in close proximity to each other. TNFα binding could then cause tighter association of the cytoplasmic domains leading to the recruitment of signaling proteins. To evaluate this hypothesis, a novel flow cytometric approach described in Example 2 (11) was employed to analyze fluorescence resonance energy transfer (FRET) between two spectral variants of GFP, cyan fluorescent protein (CFP) as the fluorescence donor and yellow fluorescent protein (YFP) as the fluorescence acceptor (12). FRET is a powerful approach to measure molecular interactions in living cells. Since energy transfer is rapidly attenuated as the distance between fluorophores increases, FRET between GFP variants allows the detection of molecular interactions within 100 Å.

Chimeric proteins were generated in which the cytoplasmic regions of p60 and p80 were replaced by either CFP or YFP and tested to determine if energy transfer occurs between different receptor pairs. FRET was performed with a dual laser FACSvantage machine that excites the YFP protein at 514 nm prior to exciting the CFP protein at 413 nm. Energy transfer from CFP to YFP was then detected as emission at 546 nm. Cells were transfected with a large excess of YFP protein compared with CFP protein. FRET was then analyzed on the CFP positive populations using the program Flowjo (Treestar Inc.).

Figure 2B:
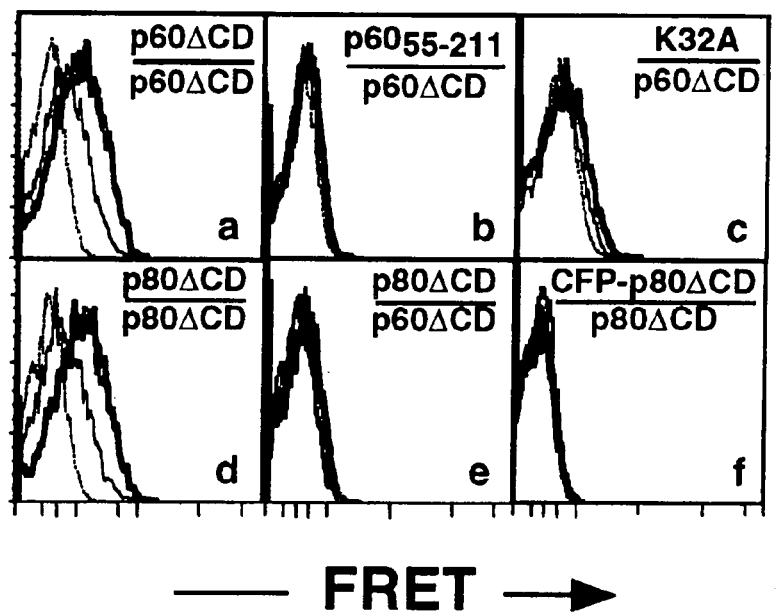
FIG. 2B illustrates homotypic self-association of p60 and p80 TNFRs as demonstrated by fluorescence resonance energy transfer (FRET). Histograms of flow cytometric analysis of 293T cells transfected with the indicated CFP (top) and YFP (bottom) plasmid pairs. The dashed line represents the CFP transfected alone control, the solid line represents FRET without TNFα and the thick line represents FRET with TNFα. The x-axis and y-axis show the FRET fluorescence intensity and cell number respectively. FRET was analyzed in the CFP positive population in which all cells were YFP positive as well. FRET is defined as fluorescence emission of YFP due to excitation of CFP. The results are representative of four independent experiments.

Energy transfer between p60ΔCD-CFP and p60ΔCD-YFP which increased substantially following the addition of TNFα (FIG. 2B, panel a) was observed. This FRET was abolished by deletion of the PLAD or by the K32A mutation that prevented PLAD association (FIG. 2B, panels b and c). Similar analyses of the p80ΔCD-CFP:p80ΔCD-YFP pair revealed a strong FRET signal that again increased with TNFα addition (FIG. 2B, panel d). Controls using p60ΔCD-YFP as acceptor for p80ΔCD-CFP or CFP-p80ΔCD (CFP fused to N-terminus of the extracellular domain) as donor showed no FRET (FIG. 2B, panels e and f). Together, these data demonstrate in living cells that the p60 and p80 chains are in close proximity to themselves and that ligand induces a change in the complexes that leads to tighter association of the CFP and YFP moieties in the cytoplasm.

Figures 3A, 3C:
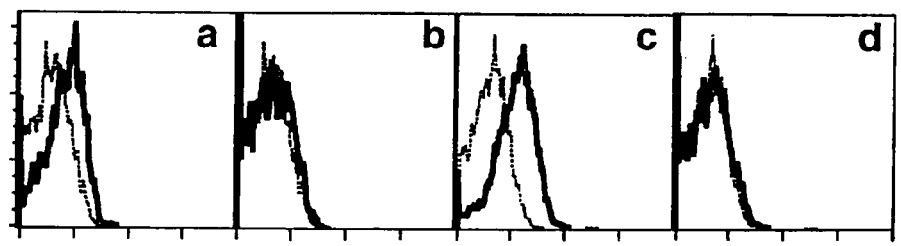
FIG. 3A show a sequence alignment of CRD1 for representatives of the TNFR superfamily. Identical residues are coded red and chemically conservative residues are coded green (26). This figure illustrates the highly conserved positions of cysteines that for disulfide bonds and define the cysteine-rich domain which confers membership in the TNFR superfamily.
FIG. 3C shows flow cytometric analysis of specific receptor association of DR4 and CD40 as demonstrated by FRET. Transfections with the indicated CFP (top) and YFP (bottom) plasmid pairs were performed as in FIG. 2B. The dashed lines represent background FRET with CFP alone and the thick lines represent FRET in the presence of both CFP and YFP fusion proteins. For each group, the x-axis is the FRET intensity and the y-axis is the cell number.

Comparison of the PLAD of p60 and p80 with the first CRD of a number of receptors in the TNFR family reveals conservation beyond the cysteines that form the disulfide bond scaffold of the domain (FIG. 3A, Y23, P36, G37 and T50 in p80). Certain other TNFR-like receptors including DR4 and Fas show less conservation in the CRD1, raising the question of whether a PLAD-like domain exists in these receptors. Whether or not ligand-independent self-association occurs in other members of the TNFR superfamily was explored.

Figure 3B:
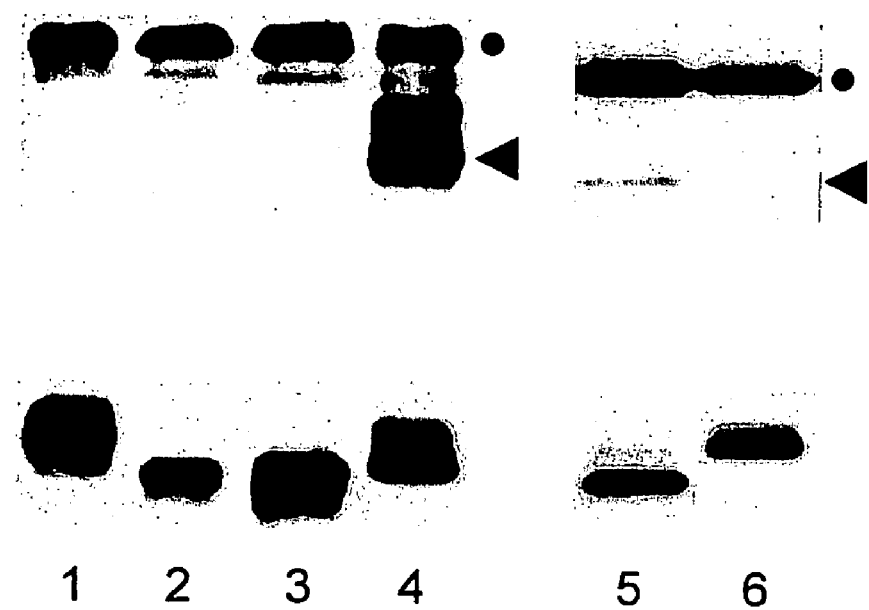
FIG. 3B illustrates receptor self-association in other TNFR superfamily members. 293T cells were transfected with either DR4ΔCD-GFP-HA (lanes 1–4) or CD40ΔCD-GFP-HA (lanes 5, 6) together with p80ΔCD-HA (lanes 1, 6), p60ΔCD-HA (lane 2), HVEMΔCD-HA (lane 3), DR4ΔCD-HA (lane 4) or CD40ΔCD-HA (lane 5). Immunoprecipitations and Western blots were performed with anti-GFP and anti-HA antibodies respectively. The top panels show the precipitated proteins in the immune complexes and the bottom panels show the expression of the DCD proteins in the cell lysates. The filled circles denote the GFP fusion proteins and the arrows indicate the DCD protein in the immune complexes.

Strikingly, the ECDs of TRAIL receptor 1 (DR4) and CD40 both self-associate but do not significantly interact with ECDs from other TNFR-like receptors (FIG. 3B). These chimeras also showed homo-specific FRET (FIG. 3C). As described in Example 2, Fas (CD95/APO-1) also specifically associates with itself (11). Thus, self-assembly through the PLAD is a conserved feature of the TNFR superfamily.

This invention reveals that the p60 and p80 TNFRs pre-assemble into functional complexes in the absence of ligand via a novel N-terminal domain termed PLAD. This reveals how CRD1 plays a crucial role in ligand-binding and receptor signaling for p60 and p80 (10). Until now, the fundamental concept of signaling by members of the TNFR superfamily is that ligand brings monomer receptor chains into apposition in three-fold complexes which leads to recruitment of cytoplasmic signal transduction proteins (1, 3, 5, 6). This model was based largely upon the crystal structure of p60 complexed with ligand, which showed that three receptor chains embrace the trimeric ligand in its intersubunit grooves and remain at least 40 Å apart. The ligand makes contact with the elongated CRD2 and CRD3 domains whereas the CRD1 domains do not interact with ligand or with each other (5). The recent description of the structure of DR5/TRAIL complex reveals similar receptor-ligand interactions (13). However, the liganded structure does not appear to reflect the receptor structure prior to ligand binding. It is now clear that p60 and p80 self-associate on the cell surface and are only found as monomers if the PLAD is deleted. Cross-linking the endogenous p60 and p80 receptors suggests that trimers are a favored conformation, but other oligomeric complexes may also occur.

Figure 3D:
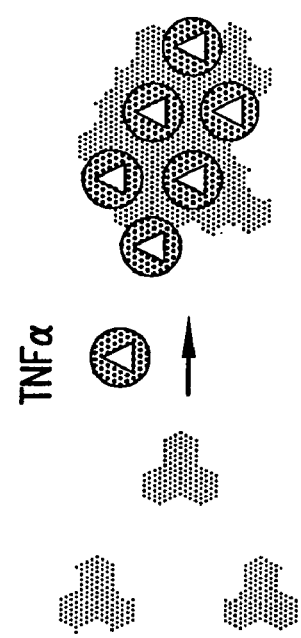
FIG. 3D illustrates the two models of TNFR signaling based on pre-associated trimer complexes. For the pre-assembly chain rearrangement model (left), the ovals represent CRDs (CRDs are numbered 1–4 going from membrane distal to membrane proximal) and stippled boxes indicate the cytoplasmic domains. The receptors are viewed perpendicular to the plasma membrane. The Roman numerals represent the chains in the trimer complex. For the trimer clustering model (right), the gray symbols indicate pre-assembled TNFR trimers on the cell surface and the encircled triangles represent the trimeric TNFα. The numbers 1–3 represent the three chains of receptor in the pre-assembled trimer complex. The receptors are viewed top down to the plasma membrane.
Figure 3D:
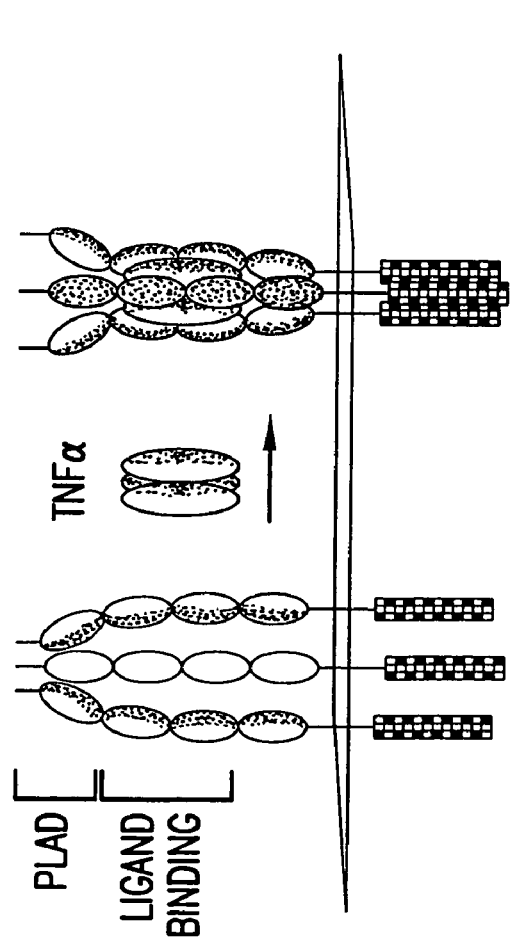

How ligand interacts with the pre-associated receptor complex is of great interest since it is now evident that pre-association is required for TNFα binding. TNFR signaling could be explained by one of two broad classes of models: 1) chain rotation and rearrangement, and 2) supercluster formation models (FIG. 3D). In chain rotation and rearrangement model, ligand intercalates into the preformed receptor trimer, causing disruption of the PLAD contacts as well as rotation and realignment of the chains into a trimer stabilized exclusively by contacts with the ligand trimer. Alternatively, ligand binding may trigger the clustering of pre-assembled TNFR trimers in which the PLAD contacts are not fully disrupted. The presence of PLAD-mediated pre-assembled TNFR trimers sheds new light on important aspects of signaling by this large family of receptors, many of which are known to be critical for lymphocyte function and homeostasis (2). Specific homotypic ECD contacts and conservation of key residues in the PLAD are characteristic of members of the TNFR superfamily including receptors that signal through death domains (p60, DR4 and Fas) and those that do not (p80 and CD40). The pre-sorting of chains into homotypic complexes on the cell surface could promote the efficiency and specificity of response. "Receptor interference" in which, for example, a p80 chain (lacking a death domain) is recruited by TNFα into a complex with p60 and causes dominant inhibition of apoptosis would be avoided. The fact that p80 actually enhances p60-induced apoptosis by providing an independent pro-apopototic signal supports this notion (15). Preformed trimers may also circumvent the requirement to sequentially recruit receptor chains to "build" a complex as might be required by the conventional model, thus accounting for the rapid signaling achieved through TNFR-like receptors (3).

Pre-assembly has been described for other receptor families, notably IL-1 and IL-2, which are comprised of heteromers of different polypeptides (16). Of particular interest is a recent description of pre-association of the erythropoietin receptor dimers that apparently undergo a "scissors-type" movement to accommodate ligand (17). In that case, self-association of the receptor chains occurs via the same amino acid contacts that are critical for ligand binding (17). By contrast, the TNFR superfamily utilizes a dedicated self-association domain distinct from the CRD2/3 ligand contact region. Identification of the PLAD could allow new treatments of diseases caused by TNFα or related ligands through the use of therapeutics that specifically inhibit the pre-ligand assembly of TNFR-like receptors and thereby prevent signaling.

EXAMPLE II

Heterozygous mutations encoding abnormal forms of Fas (CD95/APO-1)dominantly interfere with Fas-induced lymphocyte apoptosis in the human Autoimmune Lymphoproliferative Syndrome (ALPS). This invention demonstrates that, rather than depending on ligand-induced receptor oligomerization, this stems from pre-association of wild-type and mutant Fas receptors through the extracellular domain. Pre-associated Fas receptor complexes were found to be essential for signal transduction, and were demonstrated in living cells using a novel application of FRET between variants of the Green Fluorescent Protein (GFP). These results provide a new molecular mechanism for Fas signaling and dominant interference in human disease.

Fas (APO-1/CD95) is a cell surface receptor that transduces apoptotic signals critical for immune homeostasis and tolerance (19–21). Fas is a 317 amino-acid type 1 membrane glycoprotein with three extracellular cysteine-rich domains (CRD) that are characteristic of the tumor necrosis factor receptor (TNFR) superfamily.

Figure 4A:
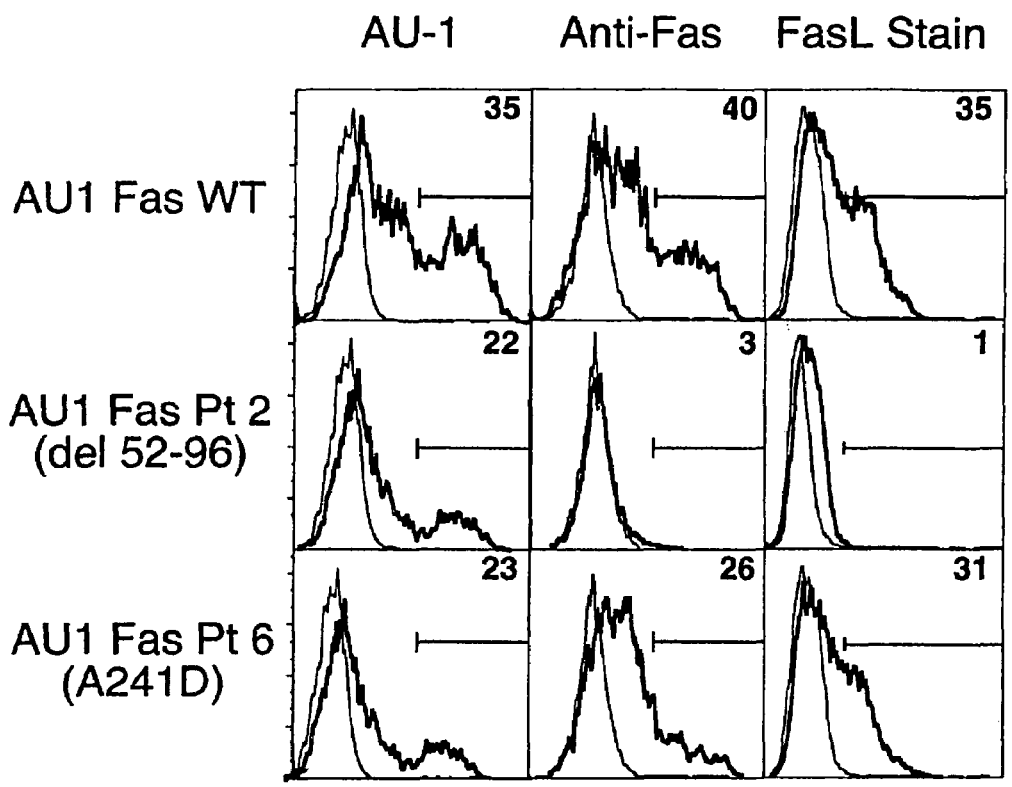
FIG. 4A shows that a pathogenic Fas mutation causes dominant-interference in the absence of ligand binding. Surface expression and binding characteristics of wild-type (WT), Pt 2 (del 52-96), and Pt 6 (A241D) Fas molecules. The left column shows surface expression 24 hours after transfection into 293T cells using staining for the AU-1 epitope tag present at the N-terminus of each receptor protein. The middle column shows the same cells stained with 10 μg/ml of the anti-Fas agonistic antibody APO-1 (Kamiya). The right column shows binding of FasL engineered to trimerize through a modified leucine zipper and visualized by staining with an anti-leucine zipper mAb (FasL stain). Antibody binding was visualized with phycoerythrin-conjugated anti-mouse antibodies. The brackets indicate the percentage of cells strongly positive for staining when compared to the non-transfected controls. In each plot the thick and thin lines represent the signals from the transfected and non-transfected cell preparations, respectively. All histograms represent 10,000 events plotted on a 4 decade logarithmic fluorescence scale (X axis) vs. cell count (Y axis). Data was collected on a FACScalibur flow cytometer using Flowjo software (Treestar software).
Figure 4B:
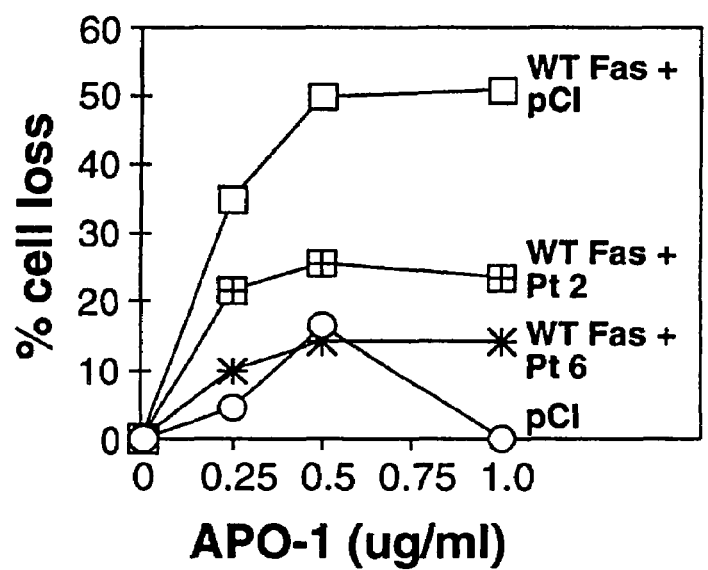
FIG. 4B shows dominant inhibition by mutant Fas molecules co-transfected with WT Fas. Ten μg of the indicated expression vectors or pCI vector alone were electroporated into BW cells lacking human Fas as previously described (15), with 5 μg of pEGFP-N1 (Clontech) to mark transfected cells with GFP. Twenty-four hours later the indicated amounts of anti-Fas mAb APO-1 were added along with 1/20 volume soluble protein A (Sigma) for maximal apoptosis induction. Apoptosis was quantitated by enumerating GFP-positive viable cells by flow cytometry and calculating cell loss (15).
Figure 4C:
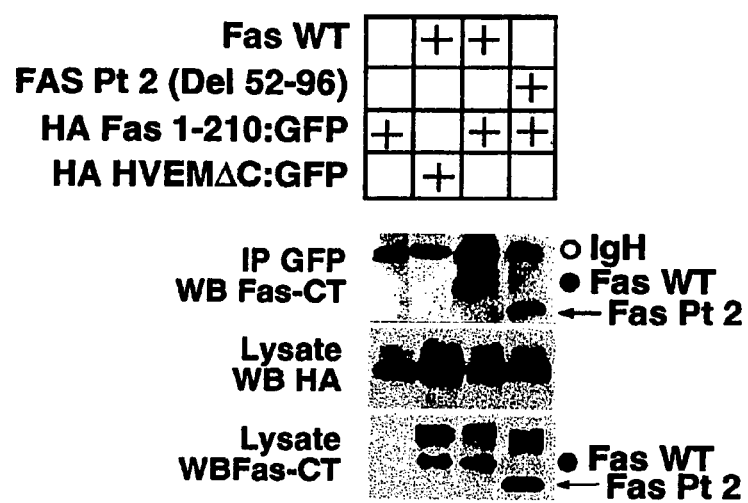
FIG. 4C illustrates self-association of Fas molecules. An expression vector encoding HA-tagged Fas with the C-terminal death domain replaced by the Green Fluorescent Protein (HAFas 1-210:GFP) was co-transfected with wild-type (WT) Fas and the EC mutant Pt 2 Fas (del 52-96). Control cells were co-transfected with WT Fas and an HA-tagged cytoplasmic truncated version of the TNF-receptor family member Herpesvirus Entry Mediator (HVEM or HveA) fused to GFP (HA HVEMΔCD:GFP). Cell lysates were lysed, immunoprecipitated with anti-GFP and electrophoresed as described in the Examples. Blots of precipitated proteins were probed with a polyclonal antiserum against the Fas C-terminal (C20, Santa Cruz biotechnology) (Anti-Fas CT) to reveal fill-length Fas molecules co-precipitating with the GFP tagged proteins. Cell lysates were also probed in western blots (WB) with anti-HA-HRP (Roche Molecular Biochemicals) and anti-Fas C20 to quantitate the total amount of these proteins. The open circle indicates the IgG heavy chain in the immunoprecipitates, the closed circle indicates WT Fas, and the arrow indicates the truncated Pt 2 Fas protein. The upper band in some lanes blotted with anti-Fas C20 represents glycosylated Fas.

In humans, lymphocytes from patients with ALPS Type 1A harboring heterozygous Fas mutations have reduced Fas-induced apoptosis, and transfection of the mutant allele causes dominant interference with apoptosis induced through Fas (29–34). This was thought to be due to ligand-mediated cross-linking of wild-type and defective Fas chains into mixed trimer complexes that cannot recruit downstream signaling molecules. However, we have studied a dominant-interfering mutation that causes an extracellular domain (ECD) deletion of most of CRD 2 (Pt 2, deletion a.a. 52–96) through altered RNA splicing. Expression of this mutant on Fas-negative 293T cells shows no binding to agonistic antibodies (FIG. 4A) (33,35). This mutant also failed to bind to trimerized FasL, while ALPS mutations in the cytoplasmic death domain, e.g. Pt 6, A241D did not affect FasL binding or APO-1 binding (FIG. 4A). Even without binding agonistic antibodies or FasL, the Pt 2 mutant dominantly interfered with Fas-induced apoptosis almost as efficiently as the Pt 6 death domain mutant (FIG. 4B). Surface staining of co-transfected cells showed no reduction in Fas expression compared to those transfected with WT Fas alone, ruling out the possibility that the mutant Fas molecules inhibited expression of the normal allele (36). Thus dominant interference cannot be explained by the conventional model of signaling by FasL-induced crosslinking of receptor monomers, because in this scheme, the Pt 2 mutant Fas molecule would not become part of a mixed receptor complex. Therefore, ligand-independent interactions between Pt 2 Fas and wild-type Fas were tested using constructs in which the cytoplasmic domain of wild-type Fas was replaced with the Green Fluorescent Protein (GFP) (HA-Fas 1-210:GFP) to avoid spurious interactions through the death domain (24,37). Both full-length and the Pt 2 Fas receptor co-precipitated with the Fas 1-210:GFP chimera in the absence of FasL (FIG. 4C). This interaction was specific, since another member of the TNFR family, the Herpesvirus Entry Mediator, fused to GFP (HVEMΔCD:GFP) did not immunoprecipitate Fas.

In order to conduct these immunoprecipitation studies, 293T cells were transfected with Fugene 6 (Boehringer Mannheim) according to the manufacturer's instructions. Cells were lysed in 150 mM NaCl, 20 mM Tris.Cl [pH 7.5], 1 mM EDTA, 5 mM iodoacetamide, 2 mM dithiothreitol (DTT), 10% glycerol, 1% TRITON X-100 and protease inhibitors (Boehringer Mannheim). After pre-clearing with protein G agarose beads (Boehringer Mannheim) and normal mouse IgG, proteins were immunoprecipitated with 1 mg anti-GFP] (Roche Molecular Biochemicals) and protein G agarose beads. Immune complexes were washed three times with lysis buffer. AU1 was immunoprecipitated with 2 µl of anti-AU1 (Covance) and protein A beads. Proteins were were electropheresed on Tris/Glycine gels (Novex), transferred to nitrocellulose membranes, and blotted with the indicated antibodies. Bands were visualized with SuperSignal WestDura (Pierce). Densitometry was performed with ID image analysis software (Kodak).

In Example I, a conserved N-terminal domain, termed the "pre-ligand assembly domain" (PLAD) is described that mediates specific self-association of other members of the TNFR superfamily. However, the N-terminus of Fas is lacking several key amino-acids conserved in other TNFR-family receptors, raising the issue of whether Fas contains a functional PLAD.

N-terminal Fas mutants truncating or eliminating the first CRD were constructed and tested for ligand binding, Fas-Fas association, and apoptotic function (FIG. 5). Fas truncation mutants were created by PCR mutagenesis with appropriate primers and Pwo high fidelity polymerase (Roche Molecular Biochemicals). For the AU-1 tagged receptors, a template with an AU-1 tag previously inserted into the region upstream of Fas CRD1 was used. For HA tagging, mutations were cloned into the EcoRI/XhoI sites of a modified pcDNA3 vector containing the leader sequence of p80 followed by an HA tag sequence. Point mutations were created with the Quickchange technique (Stratagene), substituting Pwo for Pfu polymerase. Mutations were verified by restriction enzyme mapping and automated sequencing.

Figure 5A:
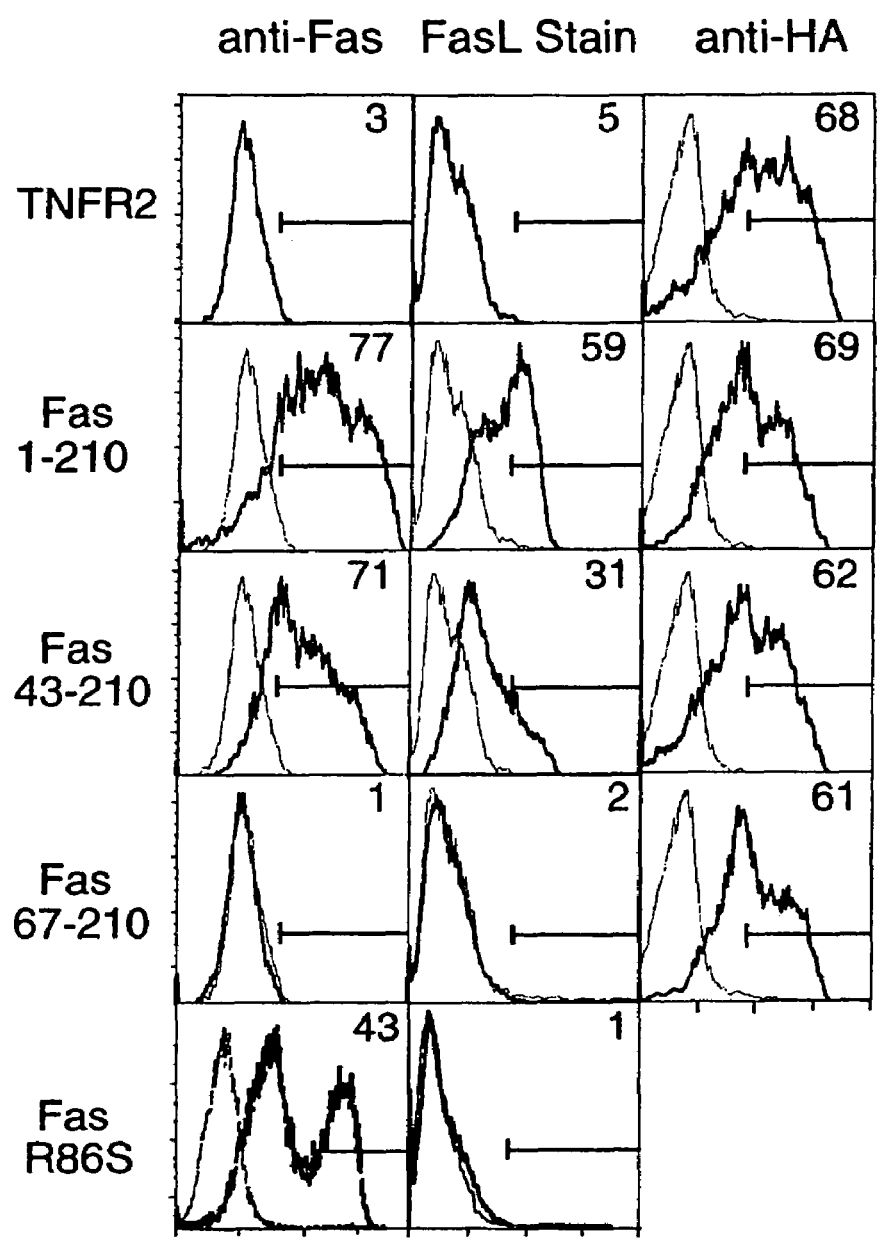
FIG. 5A shows the expression and function of Fas mutants lacking the PLAD or ligand binding. Binding of APO-1 and FasL by N-terminal Fas mutants. Staining of the indicated HA-tagged Fas mutants, the R86S Fas mutant, and control transfections with a C-terminal truncated HA-tagged TNFR2 (TNFR2) was performed as in FIG. 1A except that anti-HA was used instead of anti-AU1 to show total expression of each mutant on the cell surface.
Figure 5B:
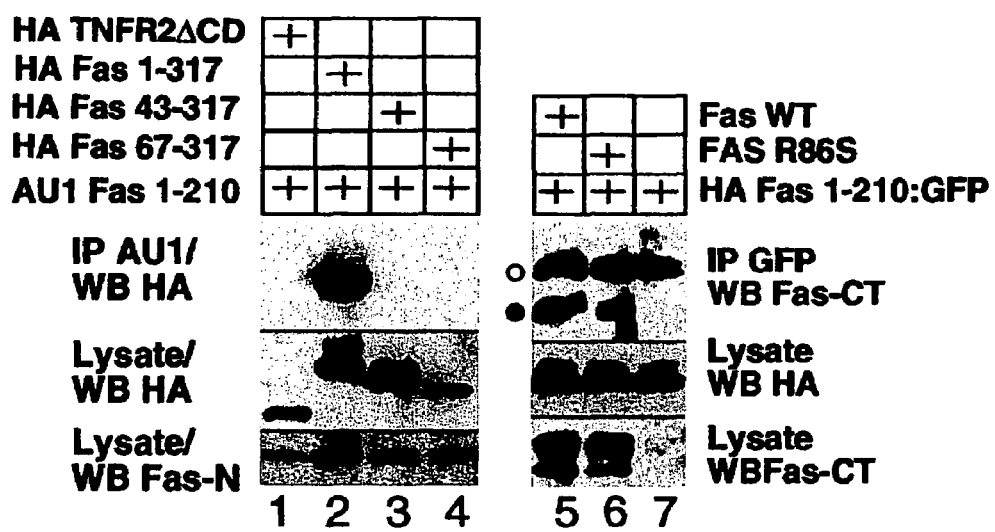
FIG. 5B shows the interaction of Fas extracellular domains is dependent on a domain in the N-terminal region of the protein. In lanes 1–4, 293T cells were co-transfected with an AU-1 tagged Fas 1-210 lacking the death domain and the indicated HA-tagged Fas mutants or control TNFR2 protein (HA TNFR2ΔCD). Lysates were immunoprecipitated with anti-AU1, and probed with anti-HA to reveal co-precipitated proteins. Control blots with an antibody against the N-terminal of Fas (WB anti-FasN) are shown to quantitate the amount of the AU-1 Fas 1-210 protein in the lysates. The results are representative of three independent transfections. Lanes 5–7 show co-precipitation of WT Fas and the FasR86S mutant by HAFas1-210:GFP with the same procedure used in FIG. 1C. The open circle indicates the Ig heavy chain of the immunoprecipitating antibody, and the closed circle indicates the position of immunoprecipitated Fas.
Figure 5C:
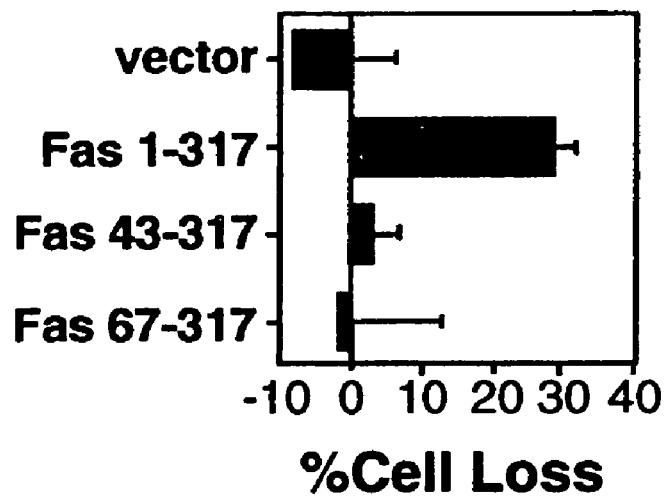
FIG. 5C illustrates the induction of apoptosis is lost in Fas molecules lacking the self-association domain. BW5147 murine thymoma cells were transfected with 10 μg of expression vectors for indicated Fas molecules. Apoptosis was induced with 500 μg/ml soluble APO-1 and quantitated as in FIG. 1B.
Figure 5D:
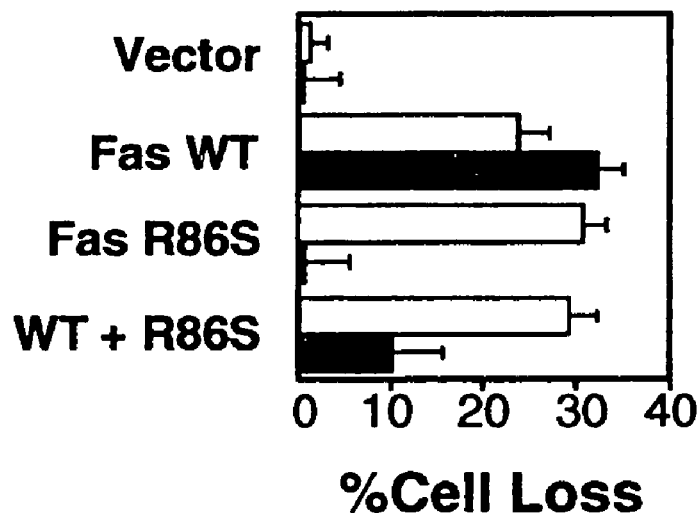
FIG. 5D illustrates the induction and inhibition of apoptosis by the non-ligand binding R86S Fas mutant. BW cells were transfected with 10 μg of each Fas expression vector and 5 μg of GFP plasmid. Apoptosis induction and quantitation was performed as in FIG. 2C, except that APO-1 was used to induce apoptosis in samples shown with open bars, and 5% v/vol FasL supernatant was added to the samples with filled bars.

These studies indicated that deleting the first 43 amino acids (a.a.) of the mature Fas protein that make up the first CRD subdomain (39) substantially reduced ligand binding but did not prevent binding of the APO-1 agonist antibody. Deleting the first 66 a.a. encoding the entire CRD1 abrogated binding of both FasL and APO-1 (FIG. 5A). Both of these deletions showed corresponding defects in apoptosis initiated by the APO-1 antibody (FIG. 5C), as well as a loss of co-precipitation of the truncated chains with a differentially tagged Fas 1-210 protein containing the complete ECD (FIG. 5B, lanes 1–4). Thus, despite partial FasL binding and normal APO-1 binding, removal of as little as 43 a.a. from the N-terminus of Fas prevented apoptosis induction, correlating with the loss of association of these truncated receptors with wild-type Fas. The loss of FasL binding by the 66 a.a. deletion (comprising CRD1) was surprising in light of the fact that most predicted contacts with FasL are found in CRD2 and CRD3 (22,23). Comparing these results with those obtained with the p60 and p80 TNFRs in Example 1, it was hypothesized that ligand-independent pre-assembly of Fas receptor complexes may be critical to allow efficient FasL binding and receptor signaling. To further explore the requirement for ligand binding in receptor self-association, a Fas point mutation, R86S, that removes a crucial CRD2 contact residue for FasL was tested (23) and does not bind FasL when expressed on the cell surface (FIG. 5A, bottom panels). The overall receptor structure was preserved, as indicated by staining by two different agonistic anti-Fas antibodies (FIG. 5A and (18)), and self-association with intact Fas still occurred as shown by co-immunoprecipitation (FIG. 5B, lanes 5–7). Even more significantly, when co-expressed with the wild-type (WT) receptor, this mutant dominantly interfered with FasL-induced apoptosis without itself binding FasL (FIG. 5D, filled bars). Apoptosis induced with the APO-1 antibody in the same cells was unimpaired in all transfections indicating that both receptors were functionally expressed on the cell surface (FIG. 5D, open bars). Thus, dominant intereference is independent of ligand binding by both naturally occuring and engineered Fas mutants. Instead, Fas function correlates with the ability to self-associate.

To quantitate Fas receptor self-association in living cells, flow cytometric and microscopic assays based on fluorescence resonance energy transfer (FRET) between spectrally distinct mutants of GFP, Cyan fluorescent protein (CFP) and Yellow fluorescent protein (YFP) were developed. CFP and YFP have spectral properties favorable for FRET in that the emission maximum for CFP is near the absorption maximum for YFP (40). Since FRET between these proteins rapidly declines at distances larger than 50 Å–100 Å, the presence of FRET between CFP and YFP fusion proteins indicates close proximity of their fluorescent protein domains. When Fas receptors with C-terminal in-frame fusions to CFP and YFP (at position 210 in place of the death domain) were co-transfected into 293T HEK cells, they were appropriately expressed on the cell surface (36).

In-frame CFP and YFP fusions with Fas and other TNF family receptors were generated by standard PCR cloning techniques and correct protein expression was confirmed by western blotting and fluorescence microscopy. 293T cells were transfected with 1 µg of the indicated YFP fusion protein constructs and 2 µg of the indicated CFP constructs. 24–36 hours later cells were harvested in PBS and analyzed on a FACSvantage cytometer with a krypton laser (Spectrophysics) tuned to 413 nm for CF? and an ILT air-cooled laser tuned to 514 nm for YFP. CFP was detected with a 470 nm/20nm bandpass filter. YFP and FRET were detected with 546 nm/10 nm bandpass filters with signals from the 514 and 413 nm lasers respectively. Cells were sequentially illuminated with the 514 and 413 nm lasers so that all three signals could be detected from each cell. Compensation was applied so that there was no FRET signal visible from cells transfected with CFP or YFP alone. 50,000 events were collected from each sample and the data was analyzed by the FlowJo software package (Treestar) For FRET efficiency measurements, CFP emission intensities from co-transfected cells were measured on a fluorescence microscope before and after bleaching the YFP with 5 min illumination through a 505–545 nm bandpass filter. Controls showed that this much intensity bleached YFP essentially completely, with very little direct bleaching of CFP. Such direct bleaching was corrected for. FRET efficiencies were calculated using the formula $$E\% = [1-(\text{CFP emission before YFP-bleach}/\text{CFP emission after YFP bleach})]*100\%.$$

Figure 6A:
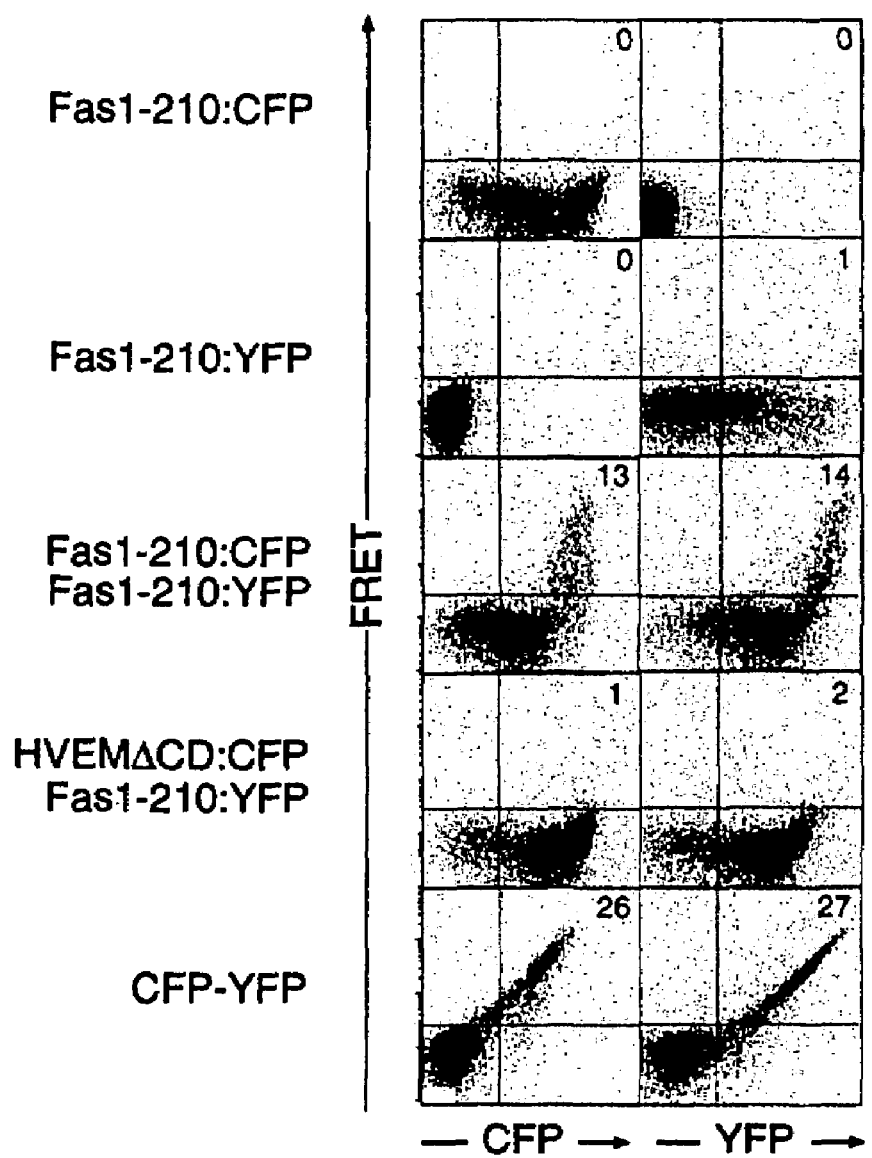
FIG. 6A shows Fluorescence Resonance Energy Transfer between Fas molecules. Dot plots showing the relationships between CFP, YFP and FRET signals in the indicated co-transfectants. CFP and YFP fusion proteins were constructed, transfected into 293T cells and analyzed on a FACS vantage cytometer. Numbers are the percentage of cells positive for CFP or YFP with FRET signal (top right quadrant).
Figure 6B:
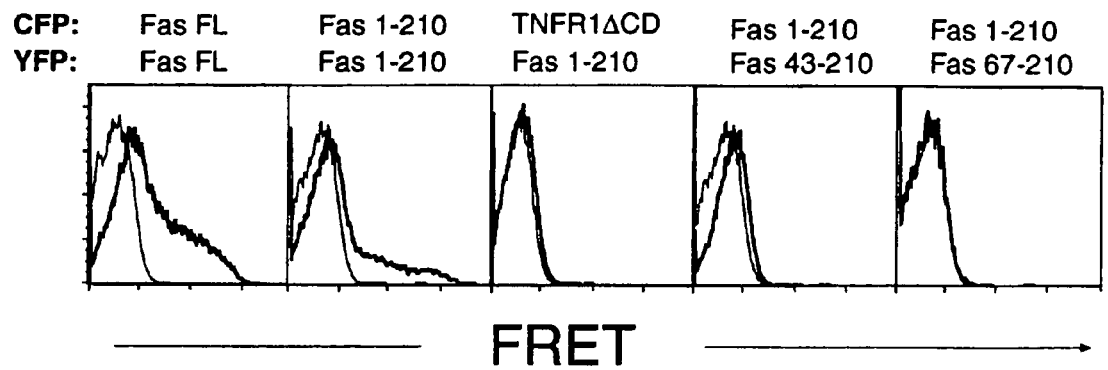
FIG. 6B is a comparison of FRET signals between full-length and N-terminal deleted Fas receptors. Histograms of FRET signals were generated in cells gated for CFP fluorescence. YFP fluorescence was comparable between all transfectants. The thick line is the signal from co-transfected cells and the thin line is the signal from the CFP construct alone of each pair.
Figure 6C:
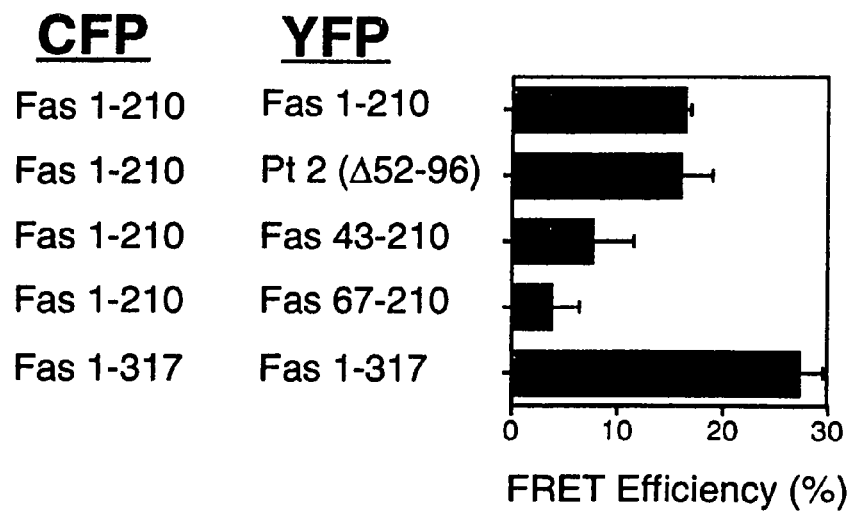
FIG. 6C shows FRET efficiency for the indicated CFP and YFP pairs as determined by microscopic photobleaching of YFP on individual cells (Five readings of 4–7 cell regions). The numbers represent the average E% and standard error for each plasmid pair.

When examined by flow cytometry, CFP excitation of cells co-transfected with the CFP and YFP Fas fusion proteins triggered strong fluorescence emission at the YFP wavelength attributable to FRET (FIG. 6A, Fas 1-210:CFP/Fas 1-210:YFP), especially at high levels of YFP expression. As a positive control, a construct in which CFP was covalently fused to YFP through a 9 a.a. peptide linker (CFP-YFP) was utilized (41). In these cells, a strong FRET signal was also detected that increased linearly with expression levels. FRET was detected between Fas fusion proteins with or without the death domain, but not between Fas and the TNF family members TNFR1 or HVEM (FIGS. 6A and B). The N-terminal truncated versions of Fas that truncate or remove the PLAD gave reduced FRET signal when co-expressed with Fas 1-210 (FIG. 6B). To quantify the FRET efficiency between these different receptor mutants, microscope-based measurements of CFP dequenching after selectively photobleaching the YFP acceptor molecule, which is another characteristic of FRET (40),24) (FIG. 6C) were made. Association of Fas lacking the death domain with itself resulted in FRET with an observed efficiency of 16%. With the death domain on both molecules, FRET efficiency rose to 27%, indicative of the oligomerization property of the death domain (42). Pt 2 Fas gave a comparable FRET efficiency to Fas 1-210 indicating nearly normal self-association, but there was reduced signal with Fas 43-210 and no significant FRET efficiency with Fas 67-210. These results suggest that Fas molecules specifically self-associate on the cell surface and that this property is dependent on the PLAD.

Figure 7A:
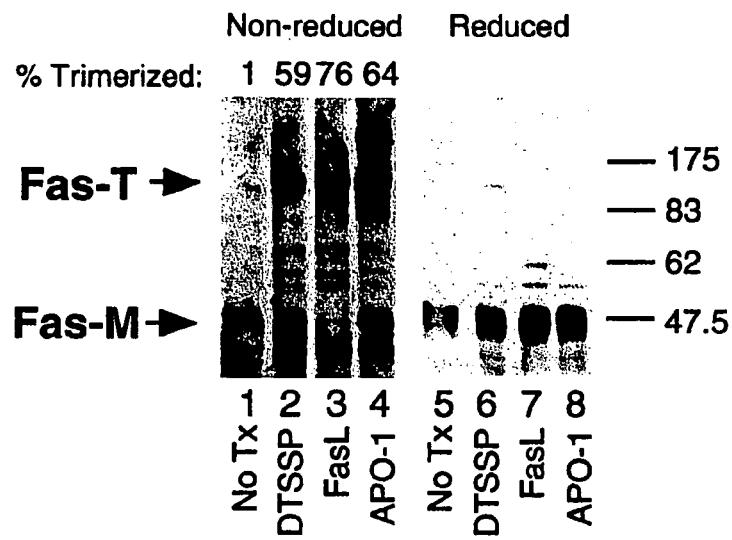
FIG. 7A illustrates pre-association of endogenous Fas receptor chains. $1 \times 10^7$ H9 lymphoma cells were treated with the crosslinker DTSSP (Pierce, 10 mM for 30 minutes at 4° C., followed by quenching with 10 mM Tris-Cl pH8 for 15 min), and/or stimulated with 1 μg of the agonistic antibody APO-1 or FasL for 15 minutes under the indicated conditions. For anti-Fas immunoblotting, cell lysates were treated with N-glycanase-F (Roche Molecular Biochemicals) before electropheresis and probed with the anti-Fas C terminal mAb B10 (Santa Cruz Biotechnology) and anti-mouse IgG1-HRP (Southern Biotechnology).
Figure 7B:
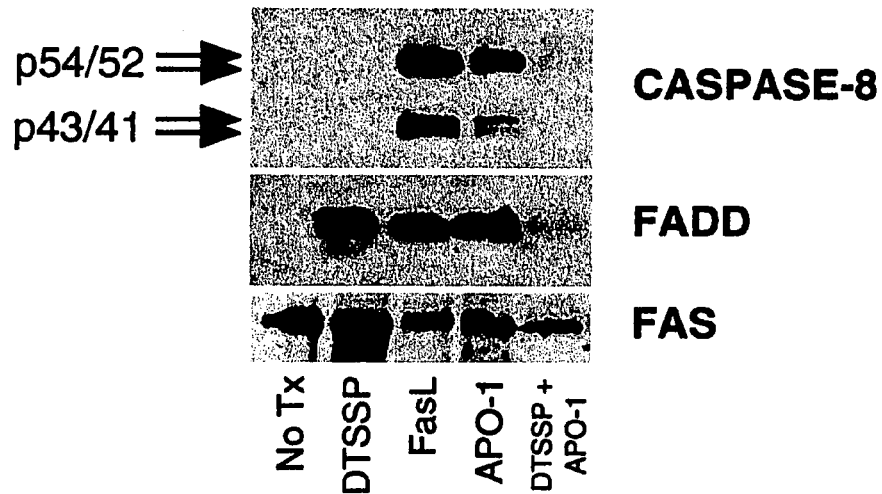
FIG. 7B After treatment with the indicated reagents, cells were lysed, immunoprecipitated and blotted for FADD and caspase-8 as previously described (11). The positions of the two isoforms of procaspase-8 (p54/52) and the caspase-8 cleavage products after proteolysis of the p11 caspase subunit (p43/41) are shown with arrows (C) PARP cleavage. Aliquots of cells used in (A) and (13) were cultured at 37° C. for an additional 4 hrs and cell lysates were blotted with anti-PARP mAb (Research Diagnostics Inc). The upper band is the 115 kD full-length PARP and the lower band is the signature 85 kD caspase cleavage fragment. The results are representative of at least three independent experiments for each condition.
Figure 7C:
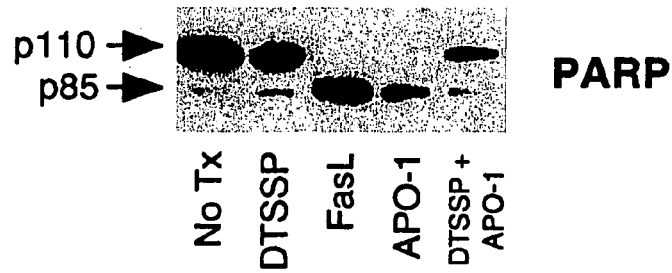

To test whether native Fas receptors self-associate on the surface of untransfected T lymphocytes, chemical cross-linking studies (FIG. 7) were performed. Addition of the cell-impermeant thiol-cleavable crosslinker 3,3'-dithiobis [sulfosuccinimidyl propionate] (DTSSP) shifted the apparent molecular weight of Fas in deglycosylated cell lysates from 45 to 140 kD, corresponding to the formation of Fas trimers (FIG. 7A, lane 2). Densitometric comparison with the monomer bands suggested that 60% of the Fas chains were cross-linked as trimers. Cleavage of the crosslinker with dithiothreitol (DTT) reduced most of these trimeric complexes to a unit state (FIG. 7A, lanes 5–8). DTSSP-induced complexes were similar to those found after stimulation with the APO-1 agonistic antibody or FasL without chemical crosslinking (FIG. 7A, lanes 3–4) (25). Agonist-induced complexes were linked by intermolecular disulfide bonds, shown by reduction with DTT (FIG. 7A, lanes 7–8). Examination of immunoprecipitated Fas signaling complexes from these cells showed that antibody or ligand stimulation triggered recruitment of FADD and caspase-8 and led to proteolysis of caspase-8 into its 41 and 43 kD processed forms (FIG. 4B) as well as the caspase-dependent cleavage of poly(ADP-ribose)polymerase (PARP) (FIG. 7C). However, signaling complexes in cells treated with DTSSP showed moderate FADD association but no caspase-8 binding or processing and no PARP cleavage, indicating that chemical crosslinking of the pre-associated receptor complex is not sufficient to trigger apoptotic signaling. Interestingly, pre-treatment with DTSSP prevented the formation of active signaling complexes in response to subsequent APO-1 treatment (FIG. 7B). These results show that non-covalent pre-association of Fas receptors is not dependent on overexpression. Ligand binding triggers a change in the structure of the receptor complex associated with interchain disulfide bond formation and intracellular signaling. Chemical crosslinking of Fas receptors appears to capture pre-associated complexes in a non-signaling state.

Figure 8A:
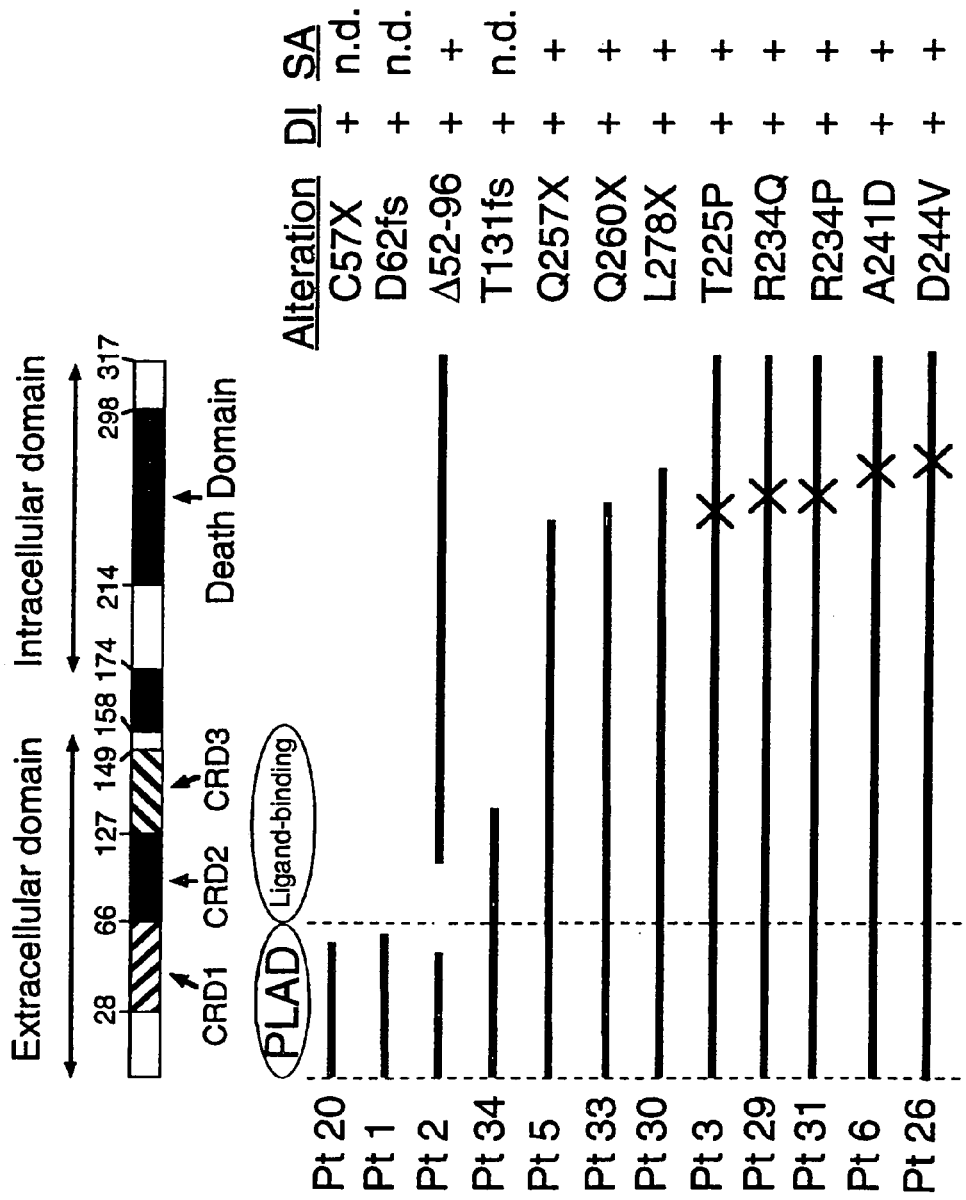
FIG. 8A illustrates that dominant interference depends on the N-terminal PLAD. Alignment of selected ALPS patient Fas mutations from families studied at the NIH. "X" symbols indicate the location of point mutations. Capacity to associate with wild-type Fas as tested by co-precipitation (SA) and dominant inhibition of Fas-induced apoptosis in co-transfection studies (DI) are indicated as shown Sequences encoding dominant-negative PLAD containing polypeptides encoded by mutations from patients #1 and #20 are shown. Numbering begins with the first amino acid after the signal peptide. Italics denote extra amino acids added by frameshift mutations.
Figure 8B:
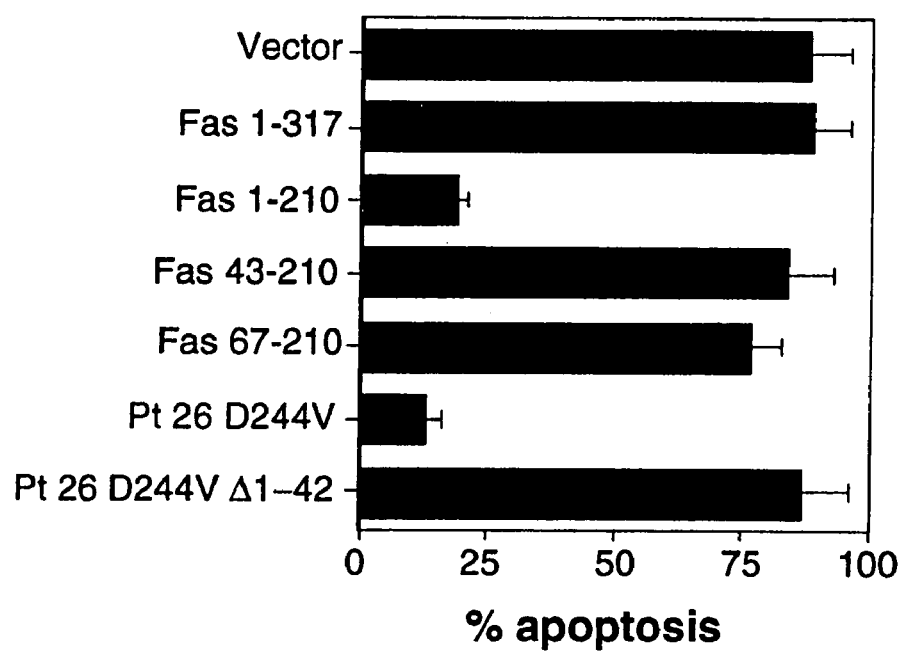
FIG. 8B shows that dominant interference is lost without the PLAD. Fas-sensitive Jurkat T lymphoma cells were transfected with the 10 μg of the indicated constructs and 2.5 μg of the GFP reporter plasmid. Eighteen hours after transfection, the indicated amounts of Apo-1 were added for 6 hours and apoptosis was quantitated by staining with Annexin V-PE (Pharmingen). Percentages are the percent of GFP(+) cells staining positive for Annexin V. These results are representative of three independent transfections.

The conserved N-terminal PLAD was required for appropriate Fas receptor function and could thus play a key role in dominant interference in ALPS. Comparing the structure, dominant interference (DI), and Fas-Fas self-association (SA) of a large number of ALPS patients that have been studied at the National Institutes of Health (29,33–35) (FIG. 8), it was found that the PLAD was preserved in every example of a dominant-interfering mutation associated with disease, including mutations that affect either the extracellular or intracellular portions of Fas. In Pts 1 and 20, mutations create premature termination polypeptides encoding only the first 57 and 62 a.a. of the mature Fas protein, suggesting that the PLAD itself was sufficient for dominant interference (FIG. 8A). Removal of all or part of the death domain (Pts 5, 30 or 33) or abrogating its FADD binding function by point mutations (Pts 3, 6, 26, 29, or 31) create potent dominant-interfering Fas molecules (29). Therefore, whether the PLAD was required for dominant interference by an engineered termination mutant of Fas that eliminates the death domain (Fas 1-210) was tested. Results indicated that both N-terminal truncations abolished dominant interference by Fas 1-210 (FIG. 8B). Truncation of the PLAD (deleting up to a.a. 42) in a Fas death domain point mutant from an ALPS patient (ALPS Pt 26, D244V) eliminated the dominant-inhibitory effect of this natural mutant (FIG. 8B).

Together these findings redefine the mechanism by which Fas mutations in ALPS dominantly interfere with normal Fas function. It is now evident that dominant-interfering Fas mutations preserve the N-terminal PLAD because this domain is responsible for complex formation between wild-type and mutant Fas molecules. The central molecular principle of genetic dominant interference is that mutant proteins must physically interact with wild-type proteins in a specific functional complex (43). Previously, dominant negative receptor mutations associated with human diseases have been shown to interfere with normal receptor signaling by sequestering ligand, blocking intracellular signaling or preventing transport of the WT chain to the cell surface (44). For Fas, we have shown that dominant interference stems from a novel mechanism involving PLAD-mediated association between wild type and mutant receptors prior to ligand binding. These findings explain why the abnormal Fas protein in ALPS Pt 2 and other Fas ECD mutants can fail to bind FasL and yet exert dominant interference sufficient to cause disease. PLAD-mediated interactions also account for the dominant-interfering interactions of the large number of ALPS patients that carry mutations affecting the death domain of Fas, since removing the PLAD abrogated the dominant negative function of Fas molecules with deleted or mutated death domains. PLAD interactions are also likely involved in the down-modulation of Fas-induced apoptosis by soluble alternatively spliced forms of Fas that all include this domain (45). Natural receptor mutants that do not encode a functional PLAD would not be expected to be dominant-interfering. PLAD-mediated dominant interference may also play a role in modulation of signaling by decoy receptors (20) and in the pathogenesis of diseases due to heterozygous genetic abnormalities in other members of the TNFR family.

These results also suggest a new model for understanding transmembrane signaling by Fas, involving conversion of pre-associated trimers to a signaling state by ligand, rather than ligand-induced oligomerization of individual receptor chains. The FRET studies allow estimation of the distance between CFP and YFP-tagged Fas molecules on the cell surface in the absence of ligand. The Förster radius, $R_0$, for randomly oriented CFP and YFP is 50 Å (23). Assuming that CFP and YFP in the fusions to Fas are equally expressed, randomly oriented with respect to each other, and randomly assorted into equilateral trimers, the observed FRET efficiencies (FIG. 3C) suggest an upper limit of 57 Å for the distance between CFP and YFP chromophores fused to full-length Fas molecules and 65 Å for fusions to Fas 1-210. These distances are much closer than what would be observed for randomly distributed molecules on the cell surface, and were specific, since FRET was not observed between Fas and other TNFR-family receptors. The fact that FRET required a threshold level of YFP expression (FIG. 3A, FAS1-210:CFP/FAS1-210:YFP) could reflect the statistics of mixing CFP-labeled and YFP-labeled Fas, or an actual dependence on receptor density for pre-association. Since we have shown that pre-association enhances Fas signaling, regulating the amount of receptor pre-association through changes in Fas expression or other means would be a novel mechanism for modulating apoptosis signaling.

Signaling through receptor complex rearrangement may be a widely-used mechanism to ensure rapid and specific cellular responses to ligands. However, this signaling mechanism also confers susceptibility to dominant interference by naturally occurring receptor variants or pathogenic heterozygous mutations in ALPS.

Throughout this application, various publications are referenced. The disclosures of these publications in their entireties are hereby incorporated by reference into this application in order to more fully describe the state of the art to which this invention pertains.

REFERENCES

1. K. J. Tracey and A. Cerami, *Annu. Rev. Cell Bio.* 9, 317 (1993); K. J. Tracey and A. Cerami, *Annu. Rev. Med.* 45, 491(1994).
2. H. Wajant, K. Pfeffer, K. Pfizenmaier and P. Scheurich, *Cytokine & Growth Factor Reviews* 9, 297 (1998); A. Ashkenazi and V. M. Dixit, *Science* 281,1305 (1998); G. G. Klaus, et al., *Int. Rev. Immunol.* 15, 5 (1997); R. Horie and T. Watanabe, *Semin. Immunol.* 10, 457 (1998).
3. M. Lenardo, et al., *Annu. Rev. Immunol.* 17,221 (1999); D. Wallach, et al., *Annu. Rev. Immunol.* 17, 331 (1999); A. M. Chinnaiyan, K. O'Rourke, M. Tewari, et al., *Cell* 81, 505 (1995); M. P. Boldin, et al., *J. Biol. Chem.* 270, 7795 (1995); M. Muzio, et al., *Cell* 85, 817 (1996); M. P. Boldin, T. M. Goncharov, Y. V. Goltsev, et al., *Cell* 85, 805 (1996); H. Hsu, J. Huang, H. Shu, et al., *Immunity* 4, 387 (1996); H. Shu, M. Takeuchi, D. V. Goeddel, *Proc. Natl. Acad. Sci. U.S.A.* 93,13973 (1996); A. T. Ting, F. X. Pimentel-Muinos, B. Seed, *EMBO J.* 15, 6189 (1996).
4. Y. Jiang, J. D. Woronicz, W. Liu, et al., *Science* 283, 543 (1999).
5. D. Banner, et al., *Cell* 73, 431 (1993).
6. L. Tartaglia, D. Goeddel, *J. Biol. Chem.* 267, 4304 (1992); H. Loetscher, et al., *J. Biol. Chem.* 266, 18324 (1991); C. A. Smith, T. Farrah, R. G. Goodwin, *Cell* 76, 959 (1994).
7. S. J. Jones, et al., *J. Immunol.* 162, 1042 (1999).
8. M. Boldin, et al., *J. Biol. Chem.* 270, 387 (1995).
9. L. Zheng and M. J. Lenardo, unpublished data.
10. S. A. Marster, A. D. Frutkin, N. J. Simpson, et al., *J. Biol. Chem.* 267, 5747 (1992); K. C. Hsu and M. V. Chao, ibid. 268, 16430 (1993); P. C. Chen, G. C. DuBois, M. Chen, ibid. 270, 2874 (1995); T. Reid, P. Louie, R. A. Heller, *Circ. Shock* 44, 84 (1994); A. E. Corcoran, et al., *Eur. J. Biochem.* 223, 831 (1994).
11. R. M. Siegel, et al. submitted.

12. L. Tron, et al., *Biophys. J.* 45, 939 (1984); J. Szollosi, et al., *Cytometry* 5, 210 (1984); R. Y. Tsien, *Annu. Rev. Biochem.* 67, 509 (1998).
13. S. G. Hymowitz, et al., *Molecular Cell* 4,563 (1999); J. Mongkolsapaya, et al., *Nature Structural Biology* 6,1048 (1999).
14. J. Naismith, T. Devine, B. J. Brandhuber, et al., *J. Biol. Chem.* 270, 13303 (1995); J. Naismith, T. Devine, T. Kohno, et al., *Structure* 4, 1251 (1996); J. Naismith, B. Brandhuber, T. Devine, et al., *J. Mol. Recog.* 9, 113 (1995).
15. F. K. Chan and M. J. Lenardo, *Eur. J. Immunol.*, (in press); R. A. Heller, K Song, N. Fan, et al., *Cell* 70, 47 (1992); T. Weiss, et al, *J. Immunol.* 158, 2398 (1997); V. Haridas, et al., *ibid.* 160, 3152 (1998); W. Declercq, et al., ibid. 161, 390 (1998).
16. C. Guo, S. K. Dower, D. Howlowka, B. Baird, *J. Biol. Chem.* 270,27562 (1995); S. Damjanovich et al., *Proc. Natl. Acad. Sci. U.S.A.* 93,13973 (1996); T. Gadella Jr. and T. M. Jovin, *J. Cell. Biol.* 129,1543 (1995).
17. O. Livnah et al., *Science* 283, 987 (1999); I. Remy, I. A. Wilson, and S. W. Michnick, *Science* 283, 990 (1999).
18. A. R Schievella, J. H. Chen, J. R. Graham, et al., *J. Biol. Chem.* 272,12069 (1997).
19. D. Wallach, et al., *Annu. Re.v Immunol.* 17, 331 (1999).
20. A. Ashkenazi, V. M. Dixit, *Science* 281, 1305 (1998).
21. M. Lenardo, et al., *Annu. Rev. Immunol.*17, 221 (1999).
22. J. R. Orlinick, A. Vaishnaw, K. B. Elkon, M. V. Chao, *J. Biol. Chem.* 272, 288–89 (1997).
23. G. C. Starling, et al., *J. Exp. Med* .185, 1487 (1997).
24. A. M. Chinnaiyan, K. O'Rourke, M. Tewari, V. M. Dixit, *Cell* 81, 505 (1995).
25. F. C. Kischkel, et al, *EMBO Journal* 14, 5579 (1995).
26. B. Huang, M. Eberstadt, E. T. Olejniczak, R. P. Meadows, S. W. Fesik, *Nature* 384, 638 (1996).
27. D. A. Martin, R. M. Siegel, L. Zheng, M. J. Lenardo, *J Biol. Chem.* 273, 4345 (1998).
28. D. Nicholson, N. Thornberry, *TIBS* 22, 299 (1997).
29. D. A. Martin, et al., *Proc. Nat.l Acad. Sci. USA* 96, 4552 (1999).
30. A. K Vaishnaw, et al., *J. Clin. Invest.* 103, 355 (1999).
31. F. Rieux-Laucat, et al., *Science* 268, 1347 (1995).
32. J. Drappa, A. K. Vaishnaw, K. E. Sullivan, J. L. Chu, K. B. Elkon, *N. Engl. J. Med.* 335, 1643 (1996).
33. G. H. Fisher, et al., *Cell* 81, 935 (1995).
34. S. E. Straus, M. Sneller, M. J. Lenardo, J. M. Puck, W. Strober, *Ann. Intern. Med.* 130, 591 (1999).
35. C. Jackson, et al., *Am. J. of Hum. Genet.* 64, 1002 (1998).
36. R. M. S and M. J. L., unpublished observations.
37. M. P. Boldin, et al., *J. Biol. Chem.* 270, 7795 (1995).
38. F. C. Chan, et. al., accompanying manuscript (1999).
39. J. H. Naismith, S. R. Sprang, *TIBS* 23, 74 (1998).
40. A. Miyawaki, R. Tsien, *Meth. Enzymol.* In Press (2000).
41. N. P. Mahajan, D. C. Harrison-Shostak, J. Michaux, B. Herman, *Chem. Biol.* 6, 401 (1999).
42. M. P. Boldin, et al., *J Biol. Chem.* 270, 387 (1995).
43. I. Herskowitz, *Nature* 329, 219 (1987).
44. E. Jouanguy, et al., *Nat Genet* 21, 370 (1999).; R. Levy-Toledano, L. H. Caro, D. Accili, S. I. Taylor, *Embo J.* 13, 835 (1994).; M. P. Cosma, M. Cardone, F. Carlomagno, V. Colantuoni, *Mol. Cell. Biol.* 18, 3321 (1998).
45. G. Papoff et al, *J Immunol.* 156, 4622 (1996).
46. W. Li, J. Schlessinger, *Mol. Cell. Biol.* 11, 3756 (1991); W. Li, E. R. Stanley, *Embo J.* 10, 277 (1991).
47. H. Walczak, et al., *Nat Med* 5, 157 (1999).

| TNFR family Receptor | | Aliases | | Accession (human Locus Link) | Human Chromosome | Mouse Chromosome | | Ligands |
|---|---|---|---|---|---|---|---|---|
| NGFR | TNFRSF16 | p75 | | M14764 (4804) | 17q21–q22 | 11 | 55.6 cM | NGF |
| Troy | TNFRSF19 | Tajα | | AF167555 (55504) | 13q12.11–12.3 | 14 | | ? |
| EDAR | | | | AF1380988 (13608) | 2q11–q13 | 10 | 29.0 cM | EDA-A1 |
| XEDAR | | EDA-A2R | | AF298812 | X | | | EDA-A2 |
| CD40 | TNFRSF5 | p50 | Bp50 | X60592 (958) | 20q12–q13.2 | 2 | 97.0 cM | CD40 Ligand |
| DcR3 | TNFRSF6B | | | AF104419 (8771) | 20q13 | | | Fas Ligand |
| FAS | TNFRSF6 | CD95 APT1 | APO-1 | M67454 (14102) | 10q24.1 | 19 | 23.0 cM | Fas Ligand |
| HveA | TNFRSF14 | HVEM TR2 | ATAR LIGHTR | U70321 (8764) | 1p36.3–p36.2 | | LIGHT | |
| OX40 | TNFRSF4 | CD134 TXGP1L | ACT35 | X75962 (7293) | 1p36 | 4 | 79.4 cM | OX40 Ligand |
| AITR | TNFRSF18 | GITR | | AF125304 (8784) | 1p36.3 | 4 | | AITR Ligand |
| CD30 | TNFRSF8 | Ki-1 | D1S166E | M83554 (943) | 1p36 | 4 | 75.5 cM | CD30 Ligand |
| 4-1BB | TNFRSF9 | CD137 | ILA | L12964 (3604) | 1p36 | 4 | 75.5 cM | 4-1BB Ligand |
| TNFR2 | TNFRSF1B | CD120b TNFBR TNF-R-II | p75 p80 TNFR2 | M32315 (7133) | 1p36.3–p36.2 | 4 | 75.5 cM | TNF Lymphotoxin |
| DR3 | TNFRSF12 | TRAMP LARD DDR3 APO-3 | WSL-1 WSL-LR TR3 | U72763 (8718) | 1p36.2 | | | ? |
| CD27 | TNFRSF7 | Tp55 | S152 | M63928 (939) | 12p13 | 6 | 60.35 cM | CD27 Ligand |
| TNFR1 | TNFRSF1A | CD120a | p55-R | M75886 | 12p13.2 | 6 | 60.55 cM | TNF |

-continued

| TNFR family Receptor | | Aliases | | Accession (human Locus Link) | Human Chromosome | Mouse Chromosome | | Ligands |
|---|---|---|---|---|---|---|---|---|
| | | TNFAR p60 | TNFR1 TNF-R-I | (7132) | | | | Lymphotoxin |
| LTβR | TNFRSF3 | CD TNFCR TNF-R-III | TNFR2-RP | L04270 (4055) | 12p13 | 6 | 60.4 cM | TNF Lymphotoxin LIGHT |
| RANK | TNFRSF11A | TRANCE-R | | AF018253 | 18q22.1 | | | RANK Ligand |
| TACI | | CAML interactor | | AF023614 (23495) | 17p11 | 11 | | Blys April |
| BCMA | TNFRSF17 | BCM | | Z29574 (608) | 16p13.1 | | | Blys April |
| DR6 | | TR7 | | NM_014452 (27242) | 6p12.1–12.2 | | | ? |
| OPG | TNFRSF11B | osteoprotegerin OCIF | TR1 | U94332 (4982) | 8q24 | | | RANK Ligand TRAIL |
| DR4 | TNFRSF10A | Apo2, | TRAILR-1 | U90875 (8797) | 8p21 | | | TRAIL |
| DR5 | TNFRSF10B | KILLER TRAIL-R2 | TRICK2A TRICKB | AF012628 (8795) | 8p22–p21 | | | TRAIL |
| DcR1 | TNFRSF10C | TRAILR3 TRID | LIT | AF012536 (8794) | 8p22–p21 | | | TRAIL |
| DcR2 | TNFRSF10D | TRUNDO | TRAILR4 | AF029761 (8793) | 8p21 | | | TRAIL |

| | MAB225* | CLONE 4.12† | TNFα BINDING‡ | SELF ASSOCIATION§ | DOMINANT INTERFERENCE‖ |
|---|---|---|---|---|---|
| p60ΔCD | 1 | 1 | 1 | + | + |
| P60$_{55-211}$ | 0.87 | 0.02 | 0.01 | NT | − |
| K19E | 1.05 | 1.07 | 1.1 | + | + |
| KY19/20AA | 0.59 | 0.14 | 0.03 | − | − |
| Q24A | 1.06 | 0.97 | 1.13 | + | + |
| K32A | 0.36 | 0.01 | 0.01 | − | − |
| DT49/50AA | 1.16 | 0.96 | 1.13 | NT | + |
| E57A | 1.68 | 0.04 | 0.02 | + | + |
| T61A | 1.42 | 1.28 | 1.35 | NT | + |
| N66F | 0.67 | 0.04 | 0.01 | + | + |
| R77A | 1.06 | 0.99 | 1.24 | NT | + |
| W108T | 1.32 | 1.11 | 1.25 | NT | + |
| L112E | 1.31 | 1.27 | 0.85 | NT | + |

*Staining of p60-specific monoclonal antibody clone MAB225 (R&D Systems). The values were normalized against the staining of HA epitope tag by dividing the percentage of MAB225 positive cells with the percentage of HA positive cells.
†Staining with p60-specific monoclonal antibody clone 4.12 (Zymed) was normalized against HA staining.
‡TNFα binding was determined by using a biotinylated form of TNFα and normalized against HA staining (25).
§Self-association was determined by immunoprecipitation assays in 293T transient transfections as described (12). NT, not tested.
‖Dominant interference was determined as described (26). Dominant inhibition by the p60ΔCD-HA mutants was at least 50% of p60ΔCD wild type (+). p60$_{55-211}$, KY19/20AA and K32A did not confer any protection (<5%) against TNF-induced death (−) in all experiments. The antibodies and TNFα binding to p60ΔCD is arbitrarily set at 1. Results are representative of three independent experiments.

What is claimed is:

1. A polypeptide comprising the isolated amino acid sequence of a pre-ligand assembly domain (PLAD) of a TNF receptor-like receptor, wherein the polypeptide is $R_1$-TNF receptor-like receptor PLAD-$R_2$, and wherein $R_1$ and $R_2$ are H, acyl, $NH_2$, or a peptide of 2–25 amino acids in length.

2. The polypeptide of claim 1, wherein the PLAD is selected from the group consisting of: the PLAD of p60, the PLAD of p80, the PLAD of Fas (CD95/APO-1), the PLAD of TRAIL, the PLAD of LTβR, the PLAD of CD40, the PLAD of CD30, the PLAD of CD27, the PLAD of HVEM, the PLAD of OX40 and the PLAD of DR4.

3. The polypeptide of claim 1, wherein the polypeptide is $R_1$-(SEQ ID NO: 1)-$R_2$, wherein $R_1$ is H, acyl, $NH_2$, or a peptide, and $R_2$ is H, acyl, $NH_2$, or a peptide of 2–25 amino acids in length.

4. The polypeptide of claim 1, wherein the polypeptide is $R_1$-(SEQ ID NO: 2)-$R_2$, wherein $R_1$ is H, acyl, $NH_2$, or a peptide, and $R_2$ is H, acyl, $NH_2$, or a peptide of 2–25 amino acids in length.

5. An isolated nucleic acid encoding the polypeptide of claim 1.

6. The isolated nucleic acid of claim 5 in a vector.

7. The vector of claim 6 in a host suitable for expressing the nucleic acid.

8. A polypeptide consisting of the amino acid sequence of a pre-ligand assembly domain of a TNF receptor-like receptor.

9. The polypeptide of claim 8, wherein the PLAD is selected from the group consisting of: the PLAD of TNF-R, the PLAD of Fas (CD95/APO-1) and the PLAD of TRAIL.

10. A method of inhibiting TNF receptor-like receptor oligomerization in a cell by administering an effective amount of the polypeptide of claim 8 or a polypeptide comprising a pre-ligand assembly domain (PLAD) of a TNF receptor-like receptor wherein the polypeptide is $R_1$-TNF receptor-like receptor PLAD-$R_2$, and wherein $R_1$ and $R_2$ are H, acyl, $NH_2$, an amino acid or a peptide of 2–25 amino acids in length.

11. A method of inhibiting ligand binding to a TNF receptor-like receptor by administering an effective amount of the polypeptide of claim 8 or a polypeptide comprising a pre-ligand assembly domain (PLAD) of a TNF receptor-like receptor wherein the polypeptide is $R_1$-TNF receptor-like receptor PLAD-$R_2$, and wherein $R_1$ and $R_2$ are H, acyl, $NH_2$, an amino acid or a peptide of 2–25 amino acids in length.

12. A method of treating inflammation in a subject by administering an effective amount of the polypeptide of claim 3 or a polypeptide comprising a pre-ligand assembly domain (PLAD) of a TNF receptor-like receptor wherein the polypeptide is $R_1$-TNF receptor-like receptor PLAD-$R_2$, and wherein $R_1$ and $R_2$ are H, acyl, $NH_2$, an amino acid or a peptide of 2–25 amino acids in length.

13. The method of claim 12, wherein the inflammation is associated with an autoimmune disorder.

14. A polypeptide comprising the isolated amino acid sequence of a pre-ligand assembly domain (PLAD) of a TNF receptor-like receptor, wherein the polypeptide is $R_1$-TNF receptor-like receptor PLAD-$R_2$, wherein $R_1$ or $R_2$ comprise an amino acid sequence that does not flank the TNF receptor-like receptor PLAD in a naturally occurring TNF receptor-like receptor.

15. A polypeptide comprising the isolated amino acid sequence of a pre-ligand assembly domain (PLAD) of a TNF receptor-like receptor, wherein the polypeptide is $R_1$-amino acids 1–43 of Fas-$R_2$ (SEQ ID NO: 3), wherein $R_1$ is H, acyl, $NH_2$, an amino acid or a peptide, and $R_2$ is H, acyl, $NH_2$, an amino acid or a peptide, and wherein the polypeptide is not a naturally occurring TNF receptor-like receptor.

16. A polypeptide comprising the isolated amino acid sequence of a pre-ligand assembly domain (PLAD) of a TNF receptor-like receptor, wherein the polypeptide is $R_1$-amino acids 1–62 of Fas-$R_2$ (SEQ ID NO: 4), wherein $R_1$ is H, acyl, $NH_2$, an amino acid or a peptide, and $R_2$ is H, acyl, $NH_2$, an amino acid or a peptide, and wherein the polypeptide is not a naturally occurring TNF receptor-like receptor.

17. A polypeptide comprising the isolated amino acid sequence of a pre-ligand assembly domain (PLAD) of a TNF receptor-like receptor, wherein the polypeptide is $R_1$-(SEQ ID NO:5)-$R_2$, wherein $R_1$ is H, acyl, $NH_2$, an amino acid or a peptide, $R_2$ is H, acyl, $NH_2$, an amino acid or a peptide, and wherein the polypeptide is not a naturally occurring TNF receptor-like receptor.

18. A polypeptide comprising the isolated amino acid sequence of a pre-ligand assembly domain (PLAD) of a TNF receptor-like receptor, wherein the polypeptide is $R_1$-(SEQ ID NO:6)-$R_2$, wherein $R_1$ is H, acyl, $NH_2$, an amino acid or a peptide, $R_2$ is H, acyl, $NH_2$, an amino acid or a peptide, and wherein the polypeptide is not a naturally occurring TNF receptor-like receptor.

19. A polypeptide comprising the isolated amino acid sequence of a pre-ligand assembly domain (PLAD) of a TNF receptor-like receptor, wherein the polypeptide is $R_1$-(SEQ ID NO: 7)-$R_2$, wherein $R_1$ is H, acyl, $NH_2$, an amino acid or a peptide, and $R_2$ is H, acyl, $NH_2$, an amino acid or a peptide, and wherein the polypeptide is not a naturally occurring TNF receptor-like receptor.

20. A polypeptide comprising the isolated amino acid sequence of a pre-ligand assembly domain (PLAD) of a TNF receptor-like receptor, wherein the polypeptide is $R_1$-amino acids 7–42 of CD27-$R_2$ (SEQ ID NO: 8), wherein $R_1$ is H, acyl, $NH_2$, an amino acid or a peptide, $R_2$ is H, acyl, $NH_2$, an amino acid or a peptide, and wherein the polypeptide is not a naturally occurring TNF receptor-like receptor.

21. A polypeptide comprising the isolated amino acid sequence of a pre-ligand assembly domain (PLAD) of a TNF receptor-like receptor, wherein the polypeptide is $R_1$-(SEQ ID NO: 9)-$R_2$, wherein $R_1$ is H, acyl, $NH_2$, an amino acid or a peptide, and $R_2$ is H, acyl, $NH_2$, an amino acid or a peptide, and wherein the polypeptide is not a naturally occurring TNF receptor-like receptor.

22. A polypeptide comprising the isolated amino acid sequence of a pre-ligand assembly domain (PLAD) of a TNF receptor-like receptor, wherein the polypeptide is $R_1$-amino acids 3–36 of OX40-$R_2$ (SEQ ID NO: 10), wherein $R_1$ is H, acyl, $NH_2$, an amino acid or a peptide, $R_2$ is H, acyl, $NH_2$, an amino acid or a peptide, and wherein the polypeptide is not a naturally occurring TNF receptor-like receptor.

23. A polyeptide comprising the isolated amino acid sequence of a pre-ligand assembly domain (PLAD) of a TNF receptor-like receptor, wherein the polypeptide is $R_1$-amino acids 109–138 of DR4-$R_2$ (SEQ ID NO: 11), wherein $R_1$ is H, acyl, $NH_2$, an amino acid or a peptide, $R_2$ is H, acyl, $NH_2$, an amino acid or a peptide, and wherein the polypeptide is not a naturally occurring TNF receptor-like receptor.

24. A method of inhibiting Fas oligomerization in a cell by administering an effective amount of a polypeptide-comprising the isolated amino acid sequence of a pre-ligand assembly domain (PLAD) of Fas, wherein the polypeptide is not a naturally occurring TNF receptor-like receptor.

25. A method of inhibiting ligand binding to Fas by administering an effective amount of a polypeptide-comprising the isolated amino acid sequence of a pre-ligand assembly domain (PLAD) of Fas, wherein the polypeptide is not a naturally occurring TNF receptor-like receptor.

* * * * *

SEQUENCE LISTING

<160> NUMBER OF SEQ ID NOS: 11

<210> SEQ ID NO 1
<211> LENGTH: 38
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 1

Cys Pro Gln Gly Lys Tyr Ile His Pro Gln Asn Asn Ser Ile Cys Cys
1               5                   10                  15

Thr Lys Cys His Lys Gly Thr Tyr Leu Tyr Asn Asp Cys Pro Gly Pro
            20                  25                  30

Gly Gln Asp Thr Asp Cys
        35

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 2

Cys Arg Leu Arg Glu Tyr Tyr Asp Gln Thr Ala Gln Met Cys Cys Ser
1               5                   10                  15

Lys Cys Ser Pro Gly Gln His Ala Lys Val Phe Cys Thr Lys Thr Ser
            20                  25                  30

Asp Thr Val Cys
        35

<210> SEQ ID NO 3
<211> LENGTH: 43
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 3

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr
        35                  40

<210> SEQ ID NO 4
<211> LENGTH: 66
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 4

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser

```
                    20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly
65

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 5

Cys Arg Asp Gln Glu Lys Glu Tyr Tyr Glu Pro Gln His Arg Ile Cys
1               5                   10                  15

Cys Ser Arg Cys Pro Pro Gly Thr Tyr Val Ser Ala Lys Cys Ser Arg
            20                  25                  30

Ile Arg Asp Thr Val Cys
        35

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 6

Cys Arg Glu Lys Gln Tyr Leu Ile Asn Ser Gln Cys Cys Ser Leu Cys
1               5                   10                  15

Gln Pro Gly Gln Lys Leu Val Ser Asp Cys Thr Glu Phe Thr Glu Thr
            20                  25                  30

Glu Cys

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 7

Cys His Gly Asn Pro Ser His Tyr Tyr Asp Lys Ala Val Arg Arg Cys
1               5                   10                  15

Cys Tyr Arg Cys Pro Met Gly Leu Phe Pro Thr Gln Gln Cys Pro Gln
            20                  25                  30

Arg Pro Thr Asp Cys Arg Lys Gln Cys
        35                  40

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence:[\]mNote =
      synthetic construct
```

-continued

```
<400> SEQUENCE: 8

Trp Trp Leu Cys Val Leu Gly Thr Leu Val Gly Leu Ser Ala Thr Pro
1               5                   10                  15

Ala Pro Lys Ser Cys Pro Glu Arg His Tyr Trp Ala Gln Gly Lys Leu
            20                  25                  30

Cys Cys Gln Met
        35

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 9

Cys Lys Glu Asp Glu Tyr Pro Val Gly Ser Glu Cys Cys Pro Lys Cys
1               5                   10                  15

Ser Pro Gly Tyr Arg Val Lys Glu Ala Cys Gly Glu Leu Thr Gly Thr
            20                  25                  30

Val Cys

<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 10

Val Gly Ala Arg Arg Leu Gly Arg Gly Pro Cys Ala Ala Leu Leu Leu
1               5                   10                  15

Leu Gly Leu Gly Leu Ser Thr Val Thr Gly Leu His Cys Val Gly Asp
            20                  25                  30

Thr Tyr

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 11

Ala Thr Ile Lys Leu His Asp Gln Ser Ile Gly Thr Gln Gln Trp Glu
1               5                   10                  15

His Ser Pro Leu Gly Glu Leu Cys Pro Pro Gly Ser His Arg
            20                  25                  30
```